US010599814B2

(12) United States Patent
Landrum et al.

(10) Patent No.: US 10,599,814 B2
(45) Date of Patent: Mar. 24, 2020

(54) DYNAMIC PAIRING OF PATIENTS TO DATA COLLECTION GATEWAYS

(71) Applicant: Medtronic Monitoring, Inc., San Jose, CA (US)

(72) Inventors: Brett A. Landrum, Shoreview, MN (US); Paul A. Fabian, Golden Valley, MN (US); Michael D. Miller, Minneapolis, MN (US); Jerry S. Wang, Blaine, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 0 days.

(21) Appl. No.: 15/227,682

(22) Filed: Aug. 3, 2016

(65) Prior Publication Data

US 2016/0371452 A1     Dec. 22, 2016

Related U.S. Application Data

(63) Continuation of application No. 12/209,278, filed on Sep. 12, 2008, now Pat. No. 9,411,936.
(Continued)

(51) Int. Cl.
*G06F 19/00* (2018.01)
*A61B 5/00* (2006.01)
(Continued)

(52) U.S. Cl.
CPC ........ *G06F 19/3418* (2013.01); *A61B 5/0006* (2013.01); *A61B 5/0022* (2013.01);
(Continued)

(58) Field of Classification Search
CPC . G06F 19/3418; G06F 19/322; A61B 5/0006; A61B 5/0022; A61B 5/02055;
(Continued)

(56) References Cited

U.S. PATENT DOCUMENTS 834,261 A   10/1906 Chambers
2,087,124 A   7/1937 Smith et al.
(Continued)

FOREIGN PATENT DOCUMENTS

AU   2003-220574 A8   10/2003
EP      1487535 A2    12/2004
(Continued)

OTHER PUBLICATIONS

Steijaert, et al., "The use of multi-frequency impedance to determine total body water and extracellular water in obese and lean female individuals", International Journal of Obesity, vol. 21 (10), Oct. 1997, pp. 930-934.
(Continued)

*Primary Examiner* — Carl H Layno
*Assistant Examiner* — Michael J Lau
(74) *Attorney, Agent, or Firm* — Shumaker & Sieffert, P.A.

(57) ABSTRACT

Systems, devices and methods transmit data from a patient device to a location, for example a remote location, where the patient is monitored. The system may comprise a server system, for example a backend server system, a gateway and the patient worn device. The gateway can be configured to communicate with the patient worn device in response to a list transmitted from the server, for example an approved patient device list transmitted from the server to the gateway. The gateway may exclude communication with patient worn devices that are not on the list. This use of the list can control data throughput from the patient device to the gateway and also from the gateway to the server, such that the communication from the device on the list to the server is maintained and appropriate information can be reliably sent from the patient device to the server.

13 Claims, 13 Drawing Sheets

Related U.S. Application Data

(60) Provisional application No. 60/972,537, filed on Sep. 14, 2007, provisional application No. 60/972,340, filed on Sep. 14, 2007, provisional application No. 60/972,336, filed on Sep. 14, 2007, provisional application No. 61/055,666, filed on May 23, 2008, provisional application No. 61/079,746, filed on Jul. 10, 2008.

(51) Int. Cl.
| | |
|---|---|
| *A61B 5/0205* | (2006.01) |
| *A61B 5/024* | (2006.01) |
| *A61B 5/0408* | (2006.01) |
| *G16H 10/60* | (2018.01) |
| *A61B 5/0402* | (2006.01) |
| *A61B 5/08* | (2006.01) |
| *A61B 5/021* | (2006.01) |
| *A61B 5/0245* | (2006.01) |
| *A61B 5/0452* | (2006.01) |
| *A61B 5/11* | (2006.01) |
| *A61B 7/00* | (2006.01) |
| *A61N 1/365* | (2006.01) |
| *A61N 1/372* | (2006.01) |

(52) U.S. Cl.
CPC ...... *A61B 5/02055* (2013.01); *A61B 5/02405* (2013.01); *A61B 5/0402* (2013.01); *A61B 5/04085* (2013.01); *A61B 5/0809* (2013.01); *A61B 5/4869* (2013.01); *A61B 5/6833* (2013.01); *A61B 5/6846* (2013.01); *G16H 10/60* (2018.01); *A61B 5/021* (2013.01); *A61B 5/02438* (2013.01); *A61B 5/02455* (2013.01); *A61B 5/0452* (2013.01); *A61B 5/0816* (2013.01); *A61B 5/1116* (2013.01); *A61B 5/1118* (2013.01); *A61B 5/7232* (2013.01); *A61B 5/7275* (2013.01); *A61B 7/003* (2013.01); *A61B 2560/0209* (2013.01); *A61B 2560/0412* (2013.01); *A61B 2562/08* (2013.01); *A61N 1/36521* (2013.01); *A61N 1/36535* (2013.01); *A61N 1/36542* (2013.01); *A61N 1/36592* (2013.01); *A61N 1/37282* (2013.01); *G06Q 2220/00* (2013.01)

(58) Field of Classification Search
CPC .............. A61B 5/02405; A61B 5/0402; A61B 5/04085; A61B 5/0809; A61B 5/4869; A61B 5/6832; A61B 5/6833; A61B 5/6846; A61B 2560/0209; A61B 2560/0412; G16H 10/60; G06Q 2220/00; A61N 1/36521; A61N 1/36535; A61N 1/36542; A61N 1/37282
USPC ........................................................ 600/300
See application file for complete search history.

(56) References Cited

U.S. PATENT DOCUMENTS

| | | |
|---|---|---|
| 2,184,511 A | 12/1939 | Bagno et al. |
| 3,170,459 A | 2/1965 | Phipps et al. |
| 3,232,291 A | 2/1966 | Parker |
| 3,370,459 A | 2/1968 | Cescati |
| 3,517,999 A | 6/1970 | Weaver |
| 3,620,216 A | 11/1971 | Szymanski |
| 3,677,260 A | 7/1972 | Funfstuck et al. |
| 3,805,769 A | 4/1974 | Sessions |
| 3,845,757 A | 11/1974 | Wyer |
| 3,874,368 A | 4/1975 | Asrican |
| 3,882,853 A | 5/1975 | Gofman et al. |
| 3,942,517 A | 3/1976 | Bowles et al. |
| 3,972,329 A | 8/1976 | Kaufman |
| 4,008,712 A | 2/1977 | Nyboer |
| 4,024,312 A | 5/1977 | Korpman |
| 4,077,406 A | 3/1978 | Sandhage et al. |
| 4,121,573 A | 10/1978 | Crovella et al. |
| 4,141,366 A | 2/1979 | Cross, Jr. et al. |
| RE30,101 E | 9/1979 | Kubicek et al. |
| 4,185,621 A | 1/1980 | Morrow |
| 4,216,462 A | 8/1980 | DiGaicomo et al. |
| 4,300,575 A | 11/1981 | Wilson |
| 4,308,872 A | 1/1982 | Watson et al. |
| 4,358,678 A | 11/1982 | Lawrence |
| 4,409,983 A | 10/1983 | Albert |
| 4,450,527 A | 5/1984 | Sramek |
| 4,451,254 A | 5/1984 | Dinius et al. |
| 4,478,223 A | 10/1984 | Allor |
| 4,498,479 A | 2/1985 | Martio et al. |
| 4,522,211 A | 6/1985 | Bare et al. |
| 4,661,103 A | 4/1987 | Harman |
| 4,664,129 A | 5/1987 | Helzel et al. |
| 4,669,480 A | 6/1987 | Hoffman |
| 4,673,387 A | 6/1987 | Phillips et al. |
| 4,681,118 A | 7/1987 | Asai et al. |
| 4,692,685 A | 9/1987 | Blaze |
| 4,699,146 A | 10/1987 | Sieverding |
| 4,721,110 A | 1/1988 | Lampadius |
| 4,730,611 A | 3/1988 | Lamb |
| 4,733,107 A | 3/1988 | O'Shaughnessy et al. |
| 4,781,200 A | 11/1988 | Baker |
| 4,793,362 A | 12/1988 | Tedner |
| 4,838,273 A | 6/1989 | Cartmell |
| 4,838,279 A | 6/1989 | Fore |
| 4,850,370 A | 7/1989 | Dower |
| 4,880,004 A | 11/1989 | Baker, Jr. et al. |
| 4,895,163 A | 1/1990 | Libke et al. |
| 4,911,175 A | 3/1990 | Shizgal |
| 4,945,916 A | 8/1990 | Kretschmer et al. |
| 4,955,381 A | 9/1990 | Way et al. |
| 4,966,158 A | 10/1990 | Honma et al. |
| 4,981,139 A | 1/1991 | Pfohl |
| 4,988,335 A | 1/1991 | Prindle et al. |
| 4,989,612 A | 2/1991 | Fore |
| 5,001,632 A | 3/1991 | Hall-Tipping |
| 5,012,810 A | 5/1991 | Strand |
| 5,025,791 A | 6/1991 | Niwa |
| 5,027,824 A | 7/1991 | Dougherty et al. |
| 5,050,612 A | 9/1991 | Matsumura |
| 5,063,937 A | 11/1991 | Ezenwa et al. |
| 5,080,099 A | 1/1992 | Way et al. |
| 5,083,563 A | 1/1992 | Collins |
| 5,086,781 A | 2/1992 | Bookspan |
| 5,113,869 A | 5/1992 | Nappholz et al. |
| 5,125,412 A | 6/1992 | Thornton |
| 5,133,355 A | 7/1992 | Strand et al. |
| 5,140,985 A | 8/1992 | Schroeder et al. |
| 5,150,708 A | 9/1992 | Brooks |
| 5,168,874 A | 12/1992 | Segalowitz |
| 5,226,417 A | 7/1993 | Swedlow et al. |
| 5,241,300 A | 8/1993 | Buschmann |
| 5,257,627 A | 11/1993 | Rapoport |
| 5,271,411 A | 12/1993 | Ripley et al. |
| 5,273,532 A | 12/1993 | Niezink et al. |
| 5,282,840 A | 2/1994 | Hudrlik |
| 5,291,013 A | 3/1994 | Nafarrate et al. |
| 5,297,556 A | 3/1994 | Shankar |
| 5,301,677 A | 4/1994 | Hsung |
| 5,319,363 A | 6/1994 | Welch et al. |
| 5,331,966 A | 7/1994 | Bennett et al. |
| 5,335,664 A | 8/1994 | Nagashima |
| 5,343,869 A | 9/1994 | Pross et al. |
| 5,353,793 A | 10/1994 | Bornn |
| 5,362,069 A | 11/1994 | Hall-Tipping |
| 5,375,604 A | 12/1994 | Kelly et al. |
| 5,411,530 A | 5/1995 | Akhtar |
| 5,437,285 A | 8/1995 | Verrier et al. |
| 5,443,073 A | 8/1995 | Wang et al. |
| 5,449,000 A | 9/1995 | Libke et al. |
| 5,450,845 A | 9/1995 | Axel |

(56) References Cited

U.S. PATENT DOCUMENTS

| | | | |
|---|---|---|---|
| 5,454,377 | A | 10/1995 | Dzwonczyk et al. |
| 5,464,012 | A | 11/1995 | Falcone |
| 5,469,859 | A | 11/1995 | Tsoglin et al. |
| 5,482,036 | A | 1/1996 | Diab et al. |
| 5,503,157 | A | 4/1996 | Sramek |
| 5,511,548 | A | 4/1996 | Riazzi |
| 5,511,553 | A | 4/1996 | Segalowitz |
| 5,518,001 | A | 5/1996 | Snell |
| 5,523,742 | A | 6/1996 | Simkins et al. |
| 5,529,072 | A | 6/1996 | Sramek |
| 5,544,661 | A | 8/1996 | Davis et al. |
| 5,558,638 | A | 9/1996 | Evers et al. |
| 5,560,368 | A | 10/1996 | Berger |
| 5,564,429 | A | 10/1996 | Bornn et al. |
| 5,564,434 | A | 10/1996 | Halperin et al. |
| 5,566,671 | A | 10/1996 | Lyons |
| 5,575,284 | A | 11/1996 | Athan et al. |
| 5,607,454 | A | 3/1997 | Cameron et al. |
| 5,632,272 | A | 5/1997 | Diab et al. |
| 5,634,468 | A | 6/1997 | Platt et al. |
| 5,642,734 | A | 7/1997 | Ruben et al. |
| 5,673,704 | A | 10/1997 | Marchlinski et al. |
| 5,678,562 | A | 10/1997 | Sellers |
| 5,687,717 | A | 11/1997 | Halpern et al. |
| 5,718,234 | A | 2/1998 | Warden et al. |
| 5,724,025 | A | 3/1998 | Tavori |
| 5,738,107 | A | 4/1998 | Martinsen et al. |
| 5,748,103 | A | 5/1998 | Flach et al. |
| 5,767,791 | A | 6/1998 | Stoop et al. |
| 5,769,793 | A | 6/1998 | Pincus et al. |
| 5,772,508 | A | 6/1998 | Sugita et al. |
| 5,772,586 | A | 6/1998 | Heinonen et al. |
| 5,778,882 | A | 7/1998 | Raymond et al. |
| 5,788,643 | A | 8/1998 | Feldman |
| 5,788,682 | A | 8/1998 | Maget, Jr. |
| 5,803,915 | A | 9/1998 | Kremenchugsky et al. |
| 5,807,272 | A | 9/1998 | Kun et al. |
| 5,814,079 | A | 9/1998 | Kieval |
| 5,817,035 | A | 10/1998 | Sullivan |
| 5,833,603 | A | 11/1998 | Kovacs et al. |
| 5,836,990 | A | 11/1998 | Li |
| 5,855,614 | A | 1/1999 | Stevens et al. |
| 5,860,860 | A | 1/1999 | Clayman |
| 5,862,802 | A | 1/1999 | Bird |
| 5,862,803 | A | 1/1999 | Besson et al. |
| 5,865,733 | A | 2/1999 | Malinouskas et al. |
| 5,876,353 | A | 3/1999 | Riff |
| 5,904,708 | A | 5/1999 | Goedeke |
| 5,935,079 | A | 8/1999 | Swanson et al. |
| 5,941,831 | A | 8/1999 | Turcott |
| 5,944,659 | A | 8/1999 | Flach et al. |
| 5,949,636 | A | 9/1999 | Johnson et al. |
| 5,957,854 | A | 9/1999 | Besson et al. |
| 5,957,861 | A | 9/1999 | Combs et al. |
| 5,964,703 | A | 10/1999 | Goodman et al. |
| 5,970,986 | A | 10/1999 | Bolz et al. |
| 5,984,102 | A | 11/1999 | Tay |
| 5,987,352 | A | 11/1999 | Klein et al. |
| 6,007,532 | A | 12/1999 | Netherly |
| 6,027,523 | A | 2/2000 | Schmieding |
| 6,045,513 | A | 4/2000 | Stone et al. |
| 6,047,203 | A | 4/2000 | Sackner et al. |
| 6,047,259 | A | 4/2000 | Campbell et al. |
| 6,049,730 | A | 4/2000 | Kristbjarnarson |
| 6,050,267 | A | 4/2000 | Nardella et al. |
| 6,050,951 | A | 4/2000 | Friedman et al. |
| 6,052,615 | A | 4/2000 | Feild et al. |
| 6,067,467 | A | 5/2000 | John |
| 6,080,106 | A | 6/2000 | Lloyd et al. |
| 6,081,735 | A | 6/2000 | Diab et al. |
| 6,095,991 | A | 8/2000 | Krausman et al. |
| 6,102,856 | A | 8/2000 | Groff et al. |
| 6,104,949 | A | 8/2000 | Pitts et al. |
| 6,112,224 | A | 8/2000 | Peifer et al. |
| 6,117,077 | A | 9/2000 | Del Mar et al. |
| 6,125,297 | A | 9/2000 | Siconolfi |
| 6,129,744 | A | 10/2000 | Boute et al. |
| 6,141,575 | A | 10/2000 | Price |
| 6,144,878 | A | 11/2000 | Schroeppel et al. |
| 6,164,284 | A | 12/2000 | Schulman et al. |
| 6,181,963 | B1 | 1/2001 | Chin et al. |
| 6,185,452 | B1 | 2/2001 | Schulman et al. |
| 6,190,313 | B1 | 2/2001 | Hinkle |
| 6,190,324 | B1 | 2/2001 | Kieval et al. |
| 6,198,394 | B1 | 3/2001 | Jacobsen et al. |
| 6,198,955 | B1 | 3/2001 | Axelgaard et al. |
| 6,208,894 | B1 | 3/2001 | Schulman et al. |
| 6,212,427 | B1 | 4/2001 | Hoover |
| 6,213,942 | B1 | 4/2001 | Flach et al. |
| 6,225,901 | B1 | 5/2001 | Kail, IV |
| 6,245,021 | B1 | 6/2001 | Stampfer |
| 6,259,939 | B1 | 7/2001 | Rogel |
| 6,267,730 | B1 | 7/2001 | Pacunas |
| 6,272,377 | B1 | 8/2001 | Sweeney et al. |
| 6,277,078 | B1 | 8/2001 | Porat et al. |
| 6,287,252 | B1 | 9/2001 | Lugo |
| 6,289,238 | B1 | 9/2001 | Besson et al. |
| 6,290,646 | B1 | 9/2001 | Cosentino et al. |
| 6,295,466 | B1 | 9/2001 | Ishikawa et al. |
| 6,305,943 | B1 | 10/2001 | Pougatchev et al. |
| 6,306,088 | B1 | 10/2001 | Krausman et al. |
| 6,308,094 | B1 | 10/2001 | Krausman et al. |
| 6,312,378 | B1 | 11/2001 | Bardy |
| 6,315,721 | B2 | 11/2001 | Schulman et al. |
| 6,327,487 | B1 | 12/2001 | Stratbucker |
| 6,330,464 | B1 | 12/2001 | Colvin, Jr. et al. |
| 6,336,903 | B1 | 1/2002 | Bardy |
| 6,339,722 | B1 | 1/2002 | Heethaar et al. |
| 6,343,140 | B1 | 1/2002 | Brooks |
| 6,347,245 | B1 | 2/2002 | Lee et al. |
| 6,358,208 | B1 | 3/2002 | Lang et al. |
| 6,385,473 | B1 | 5/2002 | Haines et al. |
| 6,398,727 | B1 | 6/2002 | Bui et al. |
| 6,400,982 | B2 | 6/2002 | Sweeney et al. |
| 6,409,674 | B1 | 6/2002 | Brockway et al. |
| 6,411,853 | B1 | 6/2002 | Millot et al. |
| 6,416,471 | B1 | 7/2002 | Kumar et al. |
| 6,440,069 | B1 | 8/2002 | Raymond et al. |
| 6,442,422 | B1 | 8/2002 | Duckert |
| 6,450,820 | B1 | 9/2002 | Palsson et al. |
| 6,450,953 | B1 | 9/2002 | Place et al. |
| 6,454,707 | B1 | 9/2002 | Casscells, III et al. |
| 6,454,708 | B1 | 9/2002 | Ferguson et al. |
| 6,459,930 | B1 | 10/2002 | Takehara et al. |
| 6,463,328 | B1 | 10/2002 | John |
| 6,473,640 | B1 | 10/2002 | Erlebacher |
| 6,480,733 | B1 | 11/2002 | Turcott |
| 6,480,734 | B1 | 11/2002 | Zhang et al. |
| 6,490,478 | B1 | 12/2002 | Zhang et al. |
| 6,491,647 | B1 | 12/2002 | Bridger et al. |
| 6,494,829 | B1 | 12/2002 | New, Jr. et al. |
| 6,496,715 | B1 | 12/2002 | Lee et al. |
| 6,512,949 | B1 | 1/2003 | Combs et al. |
| 6,520,967 | B1 | 2/2003 | Cauthen |
| 6,527,711 | B1 | 3/2003 | Stivoric et al. |
| 6,527,729 | B1 | 3/2003 | Turcott |
| 6,544,173 | B2 | 4/2003 | West et al. |
| 6,544,174 | B2 | 4/2003 | West et al. |
| 6,551,251 | B2 | 4/2003 | Zuckerwar et al. |
| 6,551,252 | B2 | 4/2003 | Sackner et al. |
| 6,569,160 | B1 | 5/2003 | Goldin et al. |
| 6,572,557 | B2 | 6/2003 | Tchou et al. |
| 6,572,636 | B1 | 6/2003 | Hagen et al. |
| 6,577,139 | B2 | 6/2003 | Cooper |
| 6,577,893 | B1 | 6/2003 | Besson et al. |
| 6,577,897 | B1 | 6/2003 | Shurubura et al. |
| 6,579,231 | B1 | 6/2003 | Phipps |
| 6,580,942 | B1 | 6/2003 | Willshire |
| 6,584,343 | B1 | 6/2003 | Ransbury et al. |
| 6,587,715 | B2 | 7/2003 | Singer |
| 6,589,170 | B1 | 7/2003 | Flach et al. |
| 6,595,927 | B2 | 7/2003 | Pitts-Crick et al. |
| 6,595,929 | B2 | 7/2003 | Stivoric et al. |
| 6,600,949 | B1 | 7/2003 | Turcott |

(56) References Cited

U.S. PATENT DOCUMENTS

| | | |
|---|---|---|
| 6,602,201 B1 | 8/2003 | Hepp et al. |
| 6,605,038 B1 | 8/2003 | Teller et al. |
| 6,611,705 B2 | 8/2003 | Hopman et al. |
| 6,616,606 B1 | 9/2003 | Petersen et al. |
| 6,622,042 B1 | 9/2003 | Thacker |
| 6,636,754 B1 | 10/2003 | Baura et al. |
| 6,641,542 B2 | 11/2003 | Cho et al. |
| 6,645,153 B2 | 11/2003 | Kroll et al. |
| 6,649,829 B2 | 11/2003 | Garber et al. |
| 6,650,917 B2 | 11/2003 | Diab et al. |
| 6,658,300 B2 | 12/2003 | Govari et al. |
| 6,659,947 B1 | 12/2003 | Carter et al. |
| 6,659,949 B1 | 12/2003 | Lang et al. |
| 6,687,540 B2 | 2/2004 | Marcovecchio |
| 6,697,658 B2 | 2/2004 | Al-Ali |
| RE38,476 E | 3/2004 | Diab et al. |
| 6,699,200 B2 | 3/2004 | Cao et al. |
| 6,701,271 B2 | 3/2004 | Willner et al. |
| 6,714,813 B2 | 3/2004 | Ishigooka et al. |
| RE38,492 E | 4/2004 | Diab et al. |
| 6,721,594 B2 | 4/2004 | Conley et al. |
| 6,728,572 B2 | 4/2004 | Hsu et al. |
| 6,748,269 B2 | 6/2004 | Thompson et al. |
| 6,749,566 B2 | 6/2004 | Russ |
| 6,751,498 B1 | 6/2004 | Greenberg et al. |
| 6,760,617 B2 | 7/2004 | Ward et al. |
| 6,773,396 B2 | 8/2004 | Flach et al. |
| 6,775,566 B2 | 8/2004 | Nissila |
| 6,790,178 B1 | 9/2004 | Mault et al. |
| 6,795,722 B2 | 9/2004 | Sheraton et al. |
| 6,814,706 B2 | 11/2004 | Barton et al. |
| 6,816,744 B2 | 11/2004 | Garfield et al. |
| 6,821,249 B2 | 11/2004 | Casscells et al. |
| 6,824,515 B2 | 11/2004 | Suorsa et al. |
| 6,827,690 B2 | 12/2004 | Bardy |
| 6,829,503 B2 | 12/2004 | Alt |
| 6,858,006 B2 | 2/2005 | MacCarter et al. |
| 6,871,211 B2 | 3/2005 | Labounty et al. |
| 6,878,121 B2 | 4/2005 | Krausman et al. |
| 6,879,850 B2 | 4/2005 | Kimball |
| 6,881,191 B2 | 4/2005 | Oakley et al. |
| 6,887,201 B2 | 5/2005 | Bardy |
| 6,890,096 B2 | 5/2005 | Tokita et al. |
| 6,893,396 B2 | 5/2005 | Schulze et al. |
| 6,894,204 B2 | 5/2005 | Dunshee |
| 6,906,530 B2 | 6/2005 | Geisel |
| 6,912,414 B2 | 6/2005 | Tong |
| 6,936,006 B2 | 8/2005 | Sarbra |
| 6,940,403 B2 | 9/2005 | Kail |
| 6,942,622 B2 | 9/2005 | Turcott |
| 6,952,695 B1 | 10/2005 | Trinks et al. |
| 6,970,742 B2 | 11/2005 | Mann et al. |
| 6,972,683 B2 | 12/2005 | Lestienne et al. |
| 6,978,177 B1 | 12/2005 | Chen et al. |
| 6,980,851 B2 | 12/2005 | Zhu et al. |
| 6,980,852 B2 | 12/2005 | Jersey-Willuhn et al. |
| 6,985,078 B2 | 1/2006 | Suzuki et al. |
| 6,987,965 B2 | 1/2006 | Ng et al. |
| 6,988,989 B2 | 1/2006 | Weiner et al. |
| 6,993,378 B2 | 1/2006 | Wiederhold et al. |
| 6,997,879 B1 | 2/2006 | Turcott |
| 7,003,346 B2 | 2/2006 | Singer |
| 7,009,362 B2 | 3/2006 | Tsukamoto et al. |
| 7,010,340 B2 | 3/2006 | Scarantino et al. |
| 7,018,338 B2 | 3/2006 | Vetter et al. |
| 7,020,508 B2 | 3/2006 | Stivoric et al. |
| 7,027,862 B2 | 4/2006 | Dahl et al. |
| 7,041,062 B2 | 5/2006 | Friedrichs et al. |
| 7,044,911 B2 | 5/2006 | Drinan et al. |
| 7,047,067 B2 | 5/2006 | Gray et al. |
| 7,050,846 B2 | 5/2006 | Sweeney et al. |
| 7,054,679 B2 | 5/2006 | Hirsh |
| 7,059,767 B2 | 6/2006 | Tokita et al. |
| 7,088,242 B2 | 8/2006 | Aupperle et al. |
| 7,113,826 B2 | 9/2006 | Henry et al. |
| 7,118,531 B2 | 10/2006 | Krill |
| 7,127,370 B2 | 10/2006 | Kelly et al. |
| 7,129,836 B2 | 10/2006 | Lawson et al. |
| 7,130,396 B2 | 10/2006 | Rogers et al. |
| 7,130,679 B2 | 10/2006 | Parsonnet et al. |
| 7,133,716 B2 | 11/2006 | Kraemer et al. |
| 7,136,697 B2 | 11/2006 | Singer |
| 7,136,703 B1 | 11/2006 | Cappa et al. |
| 7,142,907 B2 | 11/2006 | Xue et al. |
| 7,149,574 B2 | 12/2006 | Yun et al. |
| 7,149,773 B2 | 12/2006 | Haller et al. |
| 7,153,262 B2 | 12/2006 | Stivoric et al. |
| 7,156,807 B2 | 1/2007 | Carter et al. |
| 7,156,808 B2 | 1/2007 | Quy et al. |
| 7,160,252 B2 | 1/2007 | Cho et al. |
| 7,160,253 B2 | 1/2007 | Nissila et al. |
| 7,166,063 B2 | 1/2007 | Rahman et al. |
| 7,167,743 B2 | 1/2007 | Heruth et al. |
| 7,184,821 B2 | 2/2007 | Belalcazar et al. |
| 7,191,000 B2 | 3/2007 | Zhu et al. |
| 7,194,306 B1 | 3/2007 | Turcott |
| 7,206,630 B1 | 4/2007 | Tarler |
| 7,212,849 B2 | 5/2007 | Zhang et al. |
| 7,215,984 B2 | 5/2007 | Doab et al. |
| 7,215,991 B2 | 5/2007 | Besson et al. |
| 7,238,159 B2 | 7/2007 | Banet et al. |
| 7,248,916 B2 | 7/2007 | Bardy |
| 7,251,524 B1 | 7/2007 | Hepp et al. |
| 7,257,438 B2 | 8/2007 | Kinast |
| 7,261,690 B2 | 8/2007 | Teller et al. |
| 7,277,741 B2 | 10/2007 | Debreczeny et al. |
| 7,284,904 B2 | 10/2007 | Tokita et al. |
| 7,285,090 B2 | 10/2007 | Stivoric et al. |
| 7,294,105 B1 | 11/2007 | Islam |
| 7,295,879 B2 | 11/2007 | Denker et al. |
| 7,297,119 B2 | 11/2007 | Westbrook et al. |
| 7,318,808 B2 | 1/2008 | Tarassenko et al. |
| 7,319,386 B2 | 1/2008 | Collins et al. |
| 7,336,187 B2 | 2/2008 | Hubbard, Jr. et al. |
| 7,346,380 B2 | 3/2008 | Axelgaard et al. |
| 7,382,247 B2 | 6/2008 | Welch et al. |
| 7,384,398 B2 | 6/2008 | Gagnadre et al. |
| 7,390,299 B2 | 6/2008 | Weiner et al. |
| 7,395,106 B2 | 7/2008 | Ryu et al. |
| 7,423,526 B2 | 9/2008 | Despotis |
| 7,423,537 B2 | 9/2008 | Bonnet et al. |
| 7,443,302 B2 | 10/2008 | Reeder et al. |
| 7,450,024 B2 | 11/2008 | Wildman et al. |
| 7,468,032 B2 | 12/2008 | Stahmann et al. |
| 7,510,699 B2 | 3/2009 | Black et al. |
| 7,701,227 B2 | 4/2010 | Saulnier et al. |
| 7,813,778 B2 | 10/2010 | Benaron et al. |
| 7,881,763 B2 | 2/2011 | Brauker et al. |
| 7,942,824 B1 | 5/2011 | Kayyali et al. |
| 2001/0047127 A1 | 11/2001 | New, Jr. et al. |
| 2002/0004640 A1 | 1/2002 | Conn et al. |
| 2002/0019586 A1 | 2/2002 | Teller et al. |
| 2002/0019588 A1 | 2/2002 | Marro et al. |
| 2002/0028989 A1 | 3/2002 | Pelletier et al. |
| 2002/0032581 A1 | 3/2002 | Reitberg |
| 2002/0045836 A1 | 4/2002 | Alkawwas et al. |
| 2002/0088465 A1 | 7/2002 | Hill |
| 2002/0099277 A1 | 7/2002 | Harry et al. |
| 2002/0116009 A1 | 8/2002 | Fraser et al. |
| 2002/0123672 A1 | 9/2002 | Christophersom et al. |
| 2002/0123674 A1 | 9/2002 | Plicchi et al. |
| 2002/0138017 A1 | 9/2002 | Bui et al. |
| 2002/0167389 A1 | 11/2002 | Uchikoba et al. |
| 2002/0182485 A1 | 12/2002 | Anderson et al. |
| 2003/0009092 A1 | 1/2003 | Parker |
| 2003/0023184 A1 | 1/2003 | Pitts-Crick et al. |
| 2003/0028221 A1 | 2/2003 | Zhu et al. |
| 2003/0028321 A1 | 2/2003 | Brunner et al. |
| 2003/0051144 A1 | 3/2003 | Williams |
| 2003/0055460 A1 | 3/2003 | Owen et al. |
| 2003/0083581 A1 | 5/2003 | Taha et al. |
| 2003/0085717 A1 | 5/2003 | Cooper |
| 2003/0087244 A1 | 5/2003 | McCarthy |
| 2003/0092975 A1 | 5/2003 | Casscells, III et al. |

(56) References Cited

U.S. PATENT DOCUMENTS

| | | |
|---|---|---|
| 2003/0093125 A1 | 5/2003 | Zhu et al. |
| 2003/0093298 A1 | 5/2003 | Hernandez et al. |
| 2003/0100367 A1 | 5/2003 | Cooke |
| 2003/0105411 A1 | 6/2003 | Smallwood et al. |
| 2003/0135127 A1 | 7/2003 | Sackner et al. |
| 2003/0143544 A1 | 7/2003 | McCarthy |
| 2003/0149349 A1 | 8/2003 | Jensen |
| 2003/0187370 A1 | 10/2003 | Kodama |
| 2003/0191503 A1 | 10/2003 | Zhu et al. |
| 2003/0212319 A1 | 11/2003 | Magill |
| 2003/0221687 A1 | 12/2003 | Kaigler |
| 2003/0233129 A1 | 12/2003 | Matos |
| 2004/0006279 A1 | 1/2004 | Arad (Abboud) |
| 2004/0010303 A1 | 1/2004 | Bolea et al. |
| 2004/0014422 A1 | 1/2004 | Kallio |
| 2004/0015058 A1 | 1/2004 | Besson et al. |
| 2004/0019292 A1 | 1/2004 | Drinan et al. |
| 2004/0044293 A1 | 3/2004 | Burton |
| 2004/0049132 A1 | 3/2004 | Barron et al. |
| 2004/0073094 A1 | 4/2004 | Baker |
| 2004/0073126 A1 | 4/2004 | Rowlandson |
| 2004/0077954 A1 | 4/2004 | Oakley et al. |
| 2004/0100376 A1 | 5/2004 | Lye et al. |
| 2004/0102683 A1* | 5/2004 | Khanuja ............... A61B 5/0002 600/300 |
| 2004/0106951 A1 | 6/2004 | Edman et al. |
| 2004/0122489 A1 | 6/2004 | Mazar et al. |
| 2004/0127790 A1 | 7/2004 | Lang et al. |
| 2004/0133079 A1 | 7/2004 | Mazar et al. |
| 2004/0133081 A1 | 7/2004 | Teller et al. |
| 2004/0134496 A1 | 7/2004 | Cho et al. |
| 2004/0143170 A1 | 7/2004 | DuRousseau |
| 2004/0147969 A1 | 7/2004 | Mann et al. |
| 2004/0152956 A1 | 8/2004 | Korman |
| 2004/0158132 A1 | 8/2004 | Zaleski |
| 2004/0167389 A1 | 8/2004 | Brabrand |
| 2004/0172080 A1 | 9/2004 | Stadler et al. |
| 2004/0199056 A1 | 10/2004 | Husemann et al. |
| 2004/0215240 A1 | 10/2004 | Lovett et al. |
| 2004/0215247 A1 | 10/2004 | Bolz |
| 2004/0220639 A1 | 11/2004 | Mulligan et al. |
| 2004/0225199 A1 | 11/2004 | Evanyk et al. |
| 2004/0225203 A1 | 11/2004 | Jemison et al. |
| 2004/0243018 A1 | 12/2004 | Organ et al. |
| 2004/0267142 A1 | 12/2004 | Paul |
| 2005/0004506 A1 | 1/2005 | Gyory |
| 2005/0015094 A1 | 1/2005 | Keller |
| 2005/0015095 A1 | 1/2005 | Keller |
| 2005/0020935 A1 | 1/2005 | Helzel et al. |
| 2005/0027175 A1 | 2/2005 | Yang |
| 2005/0027204 A1 | 2/2005 | Kligfield et al. |
| 2005/0027207 A1 | 2/2005 | Westbrook et al. |
| 2005/0027918 A1 | 2/2005 | Govindarajulu et al. |
| 2005/0043675 A1 | 2/2005 | Pastore et al. |
| 2005/0054944 A1 | 3/2005 | Nakada et al. |
| 2005/0059867 A1 | 3/2005 | Chung |
| 2005/0065445 A1 | 3/2005 | Arzbaecher et al. |
| 2005/0065571 A1 | 3/2005 | Imran |
| 2005/0070768 A1 | 3/2005 | Zhu et al. |
| 2005/0070778 A1 | 3/2005 | Lackey et al. |
| 2005/0080346 A1 | 4/2005 | Gianchandani et al. |
| 2005/0080460 A1 | 4/2005 | Wang et al. |
| 2005/0080463 A1 | 4/2005 | Stahmann et al. |
| 2005/0085734 A1 | 4/2005 | Tehrani |
| 2005/0091338 A1 | 4/2005 | de la Huerga |
| 2005/0096513 A1 | 5/2005 | Ozguz et al. |
| 2005/0113703 A1 | 5/2005 | Farringdon et al. |
| 2005/0124878 A1 | 6/2005 | Sharony |
| 2005/0124901 A1 | 6/2005 | Misczynski et al. |
| 2005/0124908 A1 | 6/2005 | Belalcazar et al. |
| 2005/0131288 A1 | 6/2005 | Turner et al. |
| 2005/0137464 A1 | 6/2005 | Bomba |
| 2005/0137626 A1 | 6/2005 | Pastore |
| 2005/0148895 A1 | 7/2005 | Misczynski et al. |
| 2005/0158539 A1 | 7/2005 | Murphy et al. |
| 2005/0177038 A1 | 8/2005 | Kolpin et al. |
| 2005/0187482 A1 | 8/2005 | O'Brien et al. |
| 2005/0187796 A1 | 8/2005 | Rosenfeld et al. |
| 2005/0192488 A1 | 9/2005 | Bryenton et al. |
| 2005/0197654 A1 | 9/2005 | Edman et al. |
| 2005/0203433 A1 | 9/2005 | Singer |
| 2005/0203435 A1 | 9/2005 | Nakada |
| 2005/0203436 A1 | 9/2005 | Davies |
| 2005/0203637 A1 | 9/2005 | Edman et al. |
| 2005/0206518 A1 | 9/2005 | Welch et al. |
| 2005/0215914 A1 | 9/2005 | Bornzin et al. |
| 2005/0215918 A1 | 9/2005 | Frantz et al. |
| 2005/0228234 A1 | 10/2005 | Yang |
| 2005/0228238 A1 | 10/2005 | Monitzer |
| 2005/0228244 A1 | 10/2005 | Banet |
| 2005/0239493 A1 | 10/2005 | Batkin et al. |
| 2005/0240087 A1 | 10/2005 | Keenan et al. |
| 2005/0251044 A1 | 11/2005 | Hoctor et al. |
| 2005/0256418 A1 | 11/2005 | Mietus et al. |
| 2005/0261598 A1 | 11/2005 | Banet et al. |
| 2005/0261743 A1 | 11/2005 | Kroll |
| 2005/0267376 A1 | 12/2005 | Marossero et al. |
| 2005/0267377 A1 | 12/2005 | Marossero et al. |
| 2005/0267381 A1 | 12/2005 | Benditt et al. |
| 2005/0273023 A1 | 12/2005 | Bystrom et al. |
| 2005/0277841 A1 | 12/2005 | Shennib |
| 2005/0277842 A1 | 12/2005 | Silva |
| 2005/0277992 A1 | 12/2005 | Koh et al. |
| 2005/0280531 A1 | 12/2005 | Fadem et al. |
| 2005/0283197 A1 | 12/2005 | Daum et al. |
| 2005/0288601 A1 | 12/2005 | Wood et al. |
| 2006/0004300 A1 | 1/2006 | Kennedy |
| 2006/0004377 A1 | 1/2006 | Keller |
| 2006/0009697 A1 | 1/2006 | Banet et al. |
| 2006/0009701 A1 | 1/2006 | Nissila et al. |
| 2006/0010090 A1 | 1/2006 | Brockway et al. |
| 2006/0020218 A1 | 1/2006 | Freeman et al. |
| 2006/0025661 A1 | 2/2006 | Sweeney et al. |
| 2006/0030781 A1 | 2/2006 | Shennib |
| 2006/0030782 A1 | 2/2006 | Shennib |
| 2006/0031102 A1 | 2/2006 | Teller et al. |
| 2006/0041280 A1 | 2/2006 | Stahmann et al. |
| 2006/0047215 A1 | 3/2006 | Newman et al. |
| 2006/0052678 A1 | 3/2006 | Drinan et al. |
| 2006/0058543 A1 | 3/2006 | Walter et al. |
| 2006/0058593 A1 | 3/2006 | Drinan et al. |
| 2006/0064030 A1 | 3/2006 | Cosentino et al. |
| 2006/0064040 A1 | 3/2006 | Berger et al. |
| 2006/0064142 A1 | 3/2006 | Chavan et al. |
| 2006/0066449 A1 | 3/2006 | Johnson |
| 2006/0074283 A1 | 4/2006 | Henderson et al. |
| 2006/0074462 A1 | 4/2006 | Verhoef |
| 2006/0075257 A1 | 4/2006 | Martis et al. |
| 2006/0084881 A1 | 4/2006 | Korzinov et al. |
| 2006/0085049 A1 | 4/2006 | Cory et al. |
| 2006/0089679 A1 | 4/2006 | Zhu et al. |
| 2006/0094948 A1 | 5/2006 | Gough et al. |
| 2006/0102476 A1 | 5/2006 | Niwa et al. |
| 2006/0116592 A1 | 6/2006 | Zhou et al. |
| 2006/0122474 A1 | 6/2006 | Teller et al. |
| 2006/0135858 A1 | 6/2006 | Nidd et al. |
| 2006/0142654 A1 | 6/2006 | Rytky |
| 2006/0142820 A1 | 6/2006 | Von Arx et al. |
| 2006/0149168 A1 | 7/2006 | Czarnek |
| 2006/0155174 A1 | 7/2006 | Glukhovsky et al. |
| 2006/0155183 A1 | 7/2006 | Kroecker et al. |
| 2006/0155200 A1 | 7/2006 | Ng |
| 2006/0161073 A1 | 7/2006 | Singer |
| 2006/0161205 A1 | 7/2006 | Mitrani et al. |
| 2006/0161459 A9 | 7/2006 | Rosenfeld et al. |
| 2006/0167374 A1 | 7/2006 | Takehara et al. |
| 2006/0173257 A1 | 8/2006 | Nagai et al. |
| 2006/0173269 A1 | 8/2006 | Glossop |
| 2006/0195020 A1 | 8/2006 | Martin et al. |
| 2006/0195039 A1 | 8/2006 | Drew et al. |
| 2006/0195097 A1 | 8/2006 | Evans et al. |
| 2006/0195144 A1 | 8/2006 | Giftakis et al. |
| 2006/0202816 A1 | 9/2006 | Crump et al. |
| 2006/0212097 A1 | 9/2006 | Varadan et al. |

(56) References Cited

U.S. PATENT DOCUMENTS

| | | |
|---|---|---|
| 2006/0224051 A1 | 10/2006 | Teller et al. |
| 2006/0224072 A1 | 10/2006 | Shennib |
| 2006/0224079 A1 | 10/2006 | Washchuk |
| 2006/0235281 A1 | 10/2006 | Tuccillo |
| 2006/0235316 A1 | 10/2006 | Ungless et al. |
| 2006/0235489 A1 | 10/2006 | Drew et al. |
| 2006/0241641 A1 | 10/2006 | Albans et al. |
| 2006/0241701 A1 | 10/2006 | Markowitz et al. |
| 2006/0241722 A1 | 10/2006 | Thacker et al. |
| 2006/0247545 A1 | 11/2006 | St. Martin |
| 2006/0252999 A1 | 11/2006 | Devaul et al. |
| 2006/0253005 A1 | 11/2006 | Drinan et al. |
| 2006/0253044 A1 | 11/2006 | Zhang et al. |
| 2006/0258952 A1 | 11/2006 | Stahmann et al. |
| 2006/0264730 A1 | 11/2006 | Stivoric et al. |
| 2006/0264767 A1 | 11/2006 | Shennib |
| 2006/0264776 A1 | 11/2006 | Stahmann et al. |
| 2006/0271116 A1 | 11/2006 | Stahmann et al. |
| 2006/0276714 A1 | 12/2006 | Holt et al. |
| 2006/0281981 A1 | 12/2006 | Jang et al. |
| 2006/0281996 A1 | 12/2006 | Kuo et al. |
| 2006/0293571 A1 | 12/2006 | Bao et al. |
| 2006/0293609 A1 | 12/2006 | Stahmann et al. |
| 2007/0010721 A1 | 1/2007 | Chen et al. |
| 2007/0010750 A1 | 1/2007 | Ueno et al. |
| 2007/0015973 A1 | 1/2007 | Nanikashvili et al. |
| 2007/0015976 A1 | 1/2007 | Miesel et al. |
| 2007/0016089 A1 | 1/2007 | Fischell et al. |
| 2007/0021678 A1 | 1/2007 | Beck et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027388 A1 | 2/2007 | Chou |
| 2007/0027497 A1 | 2/2007 | Parnis |
| 2007/0032749 A1 | 2/2007 | Overall et al. |
| 2007/0038038 A1 | 2/2007 | Stivoric et al. |
| 2007/0038078 A1 | 2/2007 | Osadchy |
| 2007/0038255 A1 | 2/2007 | Kieval et al. |
| 2007/0038262 A1 | 2/2007 | Kieval et al. |
| 2007/0043301 A1 | 2/2007 | Martinsen et al. |
| 2007/0043303 A1 | 2/2007 | Osypka et al. |
| 2007/0048224 A1 | 3/2007 | Howell et al. |
| 2007/0060800 A1 | 3/2007 | Drinan et al. |
| 2007/0060802 A1 | 3/2007 | Ghevondian et al. |
| 2007/0073132 A1 | 3/2007 | Vosch |
| 2007/0073168 A1 | 3/2007 | Zhang et al. |
| 2007/0073181 A1 | 3/2007 | Pu et al. |
| 2007/0073361 A1 | 3/2007 | Goren et al. |
| 2007/0078687 A1* | 4/2007 | Dettinger ............ G06Q 10/10 705/3 |
| 2007/0082189 A1 | 4/2007 | Gillette |
| 2007/0083092 A1 | 4/2007 | Rippo et al. |
| 2007/0092862 A1 | 4/2007 | Gerber |
| 2007/0104840 A1 | 5/2007 | Singer |
| 2007/0106132 A1 | 5/2007 | Elhag et al. |
| 2007/0106137 A1 | 5/2007 | Baker, Jr. et al. |
| 2007/0106167 A1 | 5/2007 | Kinast |
| 2007/0118039 A1 | 5/2007 | Bodecker et al. |
| 2007/0123756 A1 | 5/2007 | Kitajima et al. |
| 2007/0123903 A1 | 5/2007 | Raymond et al. |
| 2007/0123904 A1 | 5/2007 | Stad et al. |
| 2007/0129622 A1 | 6/2007 | Bourget et al. |
| 2007/0129643 A1 | 6/2007 | Kwok et al. |
| 2007/0129769 A1 | 6/2007 | Bourget et al. |
| 2007/0142715 A1 | 6/2007 | Banet et al. |
| 2007/0142732 A1 | 6/2007 | Brockway et al. |
| 2007/0149282 A1 | 6/2007 | Lu et al. |
| 2007/0150009 A1 | 6/2007 | Kveen et al. |
| 2007/0150029 A1 | 6/2007 | Bourget et al. |
| 2007/0162089 A1 | 7/2007 | Mosesov |
| 2007/0167753 A1 | 7/2007 | Van Wyk et al. |
| 2007/0167848 A1 | 7/2007 | Kuo et al. |
| 2007/0167849 A1 | 7/2007 | Zhang et al. |
| 2007/0167850 A1 | 7/2007 | Russell et al. |
| 2007/0168461 A1* | 7/2007 | Moore ............ G06F 19/328 709/217 |
| 2007/0172424 A1 | 7/2007 | Roser |
| 2007/0173705 A1 | 7/2007 | Teller et al. |
| 2007/0180047 A1 | 8/2007 | Dong et al. |
| 2007/0180140 A1 | 8/2007 | Welch et al. |
| 2007/0191723 A1 | 8/2007 | Prystowsky et al. |
| 2007/0207858 A1 | 9/2007 | Breving |
| 2007/0208233 A1 | 9/2007 | Kovacs |
| 2007/0208235 A1 | 9/2007 | Besson et al. |
| 2007/0208262 A1 | 9/2007 | Kovacs |
| 2007/0232867 A1 | 10/2007 | Hansmann |
| 2007/0244403 A1 | 10/2007 | Natarajan et al. |
| 2007/0249946 A1 | 10/2007 | Kumar et al. |
| 2007/0250121 A1 | 10/2007 | Miesel et al. |
| 2007/0255120 A1 | 11/2007 | Rosnov |
| 2007/0255153 A1 | 11/2007 | Kumar et al. |
| 2007/0255184 A1 | 11/2007 | Shennib |
| 2007/0255531 A1 | 11/2007 | Drew |
| 2007/0260133 A1 | 11/2007 | Meyer |
| 2007/0260155 A1 | 11/2007 | Rapoport et al. |
| 2007/0260289 A1 | 11/2007 | Giftakis et al. |
| 2007/0273504 A1 | 11/2007 | Tran |
| 2007/0276273 A1 | 11/2007 | Watson, Jr. |
| 2007/0282173 A1 | 12/2007 | Wang et al. |
| 2007/0299325 A1 | 12/2007 | Farrell et al. |
| 2008/0004499 A1 | 1/2008 | Davis |
| 2008/0004904 A1 | 1/2008 | Tran |
| 2008/0021336 A1 | 1/2008 | Dobak |
| 2008/0024293 A1 | 1/2008 | Stylos |
| 2008/0024294 A1 | 1/2008 | Mazar |
| 2008/0033260 A1 | 2/2008 | Sheppard et al. |
| 2008/0039700 A1 | 2/2008 | Drinan et al. |
| 2008/0058614 A1 | 3/2008 | Banet et al. |
| 2008/0058656 A1 | 3/2008 | Costello et al. |
| 2008/0059239 A1 | 3/2008 | Gerst et al. |
| 2008/0091089 A1 | 4/2008 | Guillory et al. |
| 2008/0114220 A1 | 5/2008 | Banet et al. |
| 2008/0120784 A1 | 5/2008 | Warner et al. |
| 2008/0139934 A1 | 6/2008 | McMorrow et al. |
| 2008/0146892 A1 | 6/2008 | LeBoeuf et al. |
| 2008/0167538 A1 | 7/2008 | Teller et al. |
| 2008/0171918 A1 | 7/2008 | Teller et al. |
| 2008/0171922 A1 | 7/2008 | Teller et al. |
| 2008/0171929 A1 | 7/2008 | Katims |
| 2008/0183052 A1 | 7/2008 | Teller et al. |
| 2008/0200774 A1 | 8/2008 | Luo |
| 2008/0214903 A1 | 9/2008 | Orbach |
| 2008/0220865 A1 | 9/2008 | Hsu |
| 2008/0221399 A1 | 9/2008 | Zhou et al. |
| 2008/0221402 A1 | 9/2008 | Despotis |
| 2008/0224852 A1 | 9/2008 | Dicks et al. |
| 2008/0228084 A1 | 9/2008 | Bedard et al. |
| 2008/0275465 A1 | 11/2008 | Paul et al. |
| 2008/0287751 A1 | 11/2008 | Stivoric et al. |
| 2008/0287752 A1 | 11/2008 | Stroetz et al. |
| 2008/0293491 A1 | 11/2008 | Wu et al. |
| 2008/0294019 A1 | 11/2008 | Tran |
| 2008/0294020 A1 | 11/2008 | Sapounas |
| 2008/0318681 A1 | 12/2008 | Rofougaran et al. |
| 2008/0319279 A1 | 12/2008 | Ramsay et al. |
| 2008/0319282 A1 | 12/2008 | Tran |
| 2008/0319290 A1 | 12/2008 | Mao et al. |
| 2009/0005016 A1 | 1/2009 | Eng et al. |
| 2009/0018410 A1 | 1/2009 | Coene et al. |
| 2009/0018456 A1 | 1/2009 | Hung |
| 2009/0048526 A1 | 2/2009 | Aarts |
| 2009/0054737 A1 | 2/2009 | Magar et al. |
| 2009/0062670 A1 | 3/2009 | Sterling et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |

(56) References Cited

U.S. PATENT DOCUMENTS

| | | |
|---|---|---|
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0177145 A1 | 7/2009 | Ohlander et al. |
| 2009/0182204 A1 | 7/2009 | Semler et al. |
| 2009/0234410 A1 | 9/2009 | Libbus et al. |
| 2009/0292194 A1 | 11/2009 | Libbus et al. |
| 2010/0056881 A1 | 3/2010 | Libbus et al. |
| 2010/0191310 A1 | 7/2010 | Bly et al. |
| 2011/0144470 A1 | 6/2011 | Mazar et al. |
| 2011/0245711 A1 | 10/2011 | Katra et al. |
| 2011/0270049 A1 | 11/2011 | Katra et al. |

FOREIGN PATENT DOCUMENTS

| | | |
|---|---|---|
| EP | 1579801 A1 | 9/2005 |
| JP | 2005-521448 A | 7/2005 |
| WO | 2000/079255 A1 | 12/2000 |
| WO | 2001/089362 A2 | 11/2001 |
| WO | 2002/092101 | 11/2002 |
| WO | 2003/082080 | 10/2003 |
| WO | 2005/051164 A2 | 6/2005 |
| WO | 2005/104930 A1 | 11/2005 |
| WO | 2006/008745 A2 | 1/2006 |
| WO | 2006/102476 A2 | 9/2006 |
| WO | 2006/111878 A1 | 10/2006 |
| WO | 2007/041783 A1 | 4/2007 |
| WO | 2007/106455 A2 | 9/2007 |
| WO | 2009/116906 A1 | 9/2009 |

OTHER PUBLICATIONS

Stewart, et al., "Effects of a home-based intervention among patients with congestive heart failure discharged from acute hospital care", Arch Intern Med., vol. 158, 1998, pp. 1067-1072.

Stewart, et al., "Effects of a multidisciplinary, home-based intervention on planned readmissions and survival among patients with chronic congestive heart failure: a randomized controlled study", The Lancet, vol. 354 (9184), Sep. 1999, pp. 1077-1083.

Stewart, et al., "Home-based intervention in congestive heart failure: long-term implications on readmission and survival", Circulation, vol. 105, 2002, pp. 2861-2866.

Stewart, et al., "Prolonged beneficial effects of a home-based intervention on unplanned readmissions and mortality among patients with congestive heart failure", Arch Intern Med., vol. 159, 1999, pp. 257-261.

Stewart, et al., "Trends in Hospitalization for Heart Failure in Scotland. An Epidemic that has Reached Its Peak?", European Heart Journal, vol. 22 (3), 2001, pp. 209-217.

Swedberg, et al., "Guidelines for the diagnosis and treatment of chronic heart failure: executive summary: The task force for the diagnosis and treatment of chronic heart failure of the European Society of Cardiology", Eur Heart J., vol. 26 (11), Jun. 2005, pp. 1115-1140.

Tang, "Case studies in advanced monitoring: OptiVol", Rev Cardiovasc Med., vol. 7 Suppl 1, 2006, pp. S62-S66.

The Economist, "Something in the way he moves", retrieved from http://www.economist.com/science/printerFriendly.cfm?storyid=9861412, 2007.

The Escape Investigators, "Evaluation Study of Congestive Heart Failure and Pulmonary Artery Catheterization Effectiveness", JAMA, vol. 294, 2005, pp. 1625-1633.

Tosi, et al., "Seismic signal detection by fractal dimension analysis", Bulletin of the Seismological Society of America, vol. 89 (4), Aug. 1999, pp. 970-977.

Van De Water, et al., "Monitoring the chest with impedance", Chest, vol. 64, 1973, pp. 597-603.

Van Someren, "Actigraphic monitoring of movement and rest-activity rhythms in aging, Alzheimer's disease, and Parkinson's disease", IEEE Transactions on Rehabilitation Engineering, vol. 5 (4), Dec. 1997, pp. 394-398.

Vasan, et al., "Congestive heart failure in subjects with normal versus reduced left ventricular ejection fraction", J Am Coll Cardiol, vol. 33, 1999, pp. 1948-1955.

Verdecchia, et al., "Adverse prognostic value of an blunted circadian rhythm of heart rate in essential hypertension", Journal of Hypertension, vol. 16 (9), 1998, pp. 1335-1343.

Verdecchia, et al., "Ambulatory pulse pressure: a potent predictor of total cardiovascular risk in hypertension", Hypertension, vol. 32, 1998, pp. 983-988.

Vollmann, et al., "Clinical utility of intrathoracic impedance monitoring to alert patients with an implanted device of deteriorating chronic heart failure", European Heart Journal Advance Access, downloaded from http://eurheartj.oxfordjournals.org/cgi/content/full/ehl506v1, Feb. 19, 2007, 6 pages.

Vuksanovic, et al., "Effect of posture on heart rate variability spectral measures in children and young adults with heart disease", International Journal of Cardiology, vol. 101 (2), 2005, pp. 273-278.

Wang, et al., "Feasibility of using an implantable system to measure thoracic congestion in an ambulatory chronic heart failure canine model", PACE, vol. 28 (5), 2005, pp. 404-411.

Wickemeyer, et al., "Association between atrial and ventricular tachyarrhythmias, intrathoracic impedance and heart failure decompensation in CRT-D Patients", Journal of Cardiac Failure, vol. 13 (6), 2007, pp. S131-S132.

Williams, et al., "How do different indicators of cardiac pump function impact upon the long-term prognosis of patients with chronic heart failure", American Heart Journal, vol. 150 (5), date unknown, pp. E1-E983.

Wonisch, et al., "Continuous hemodynamic monitoring during exercise in patients with pulmonary hypertension", Int J Cardiol., vol. 101 (3), Jun. 8, 2005, pp. 415-420.

Wynne, et al., "Impedance cardiography: a potential monitor for hemodialysis", Journal of Surgical Research, vol. 133 (1), 2006, pp. 55-60.

Yancy, "Current approaches to monitoring and management of heart failure", Rev Cardiovasc Med., vol. 7 Suppl 1, 2006, pp. S25-S32.

Ypenburg, et al., "Intrathoracic Impedance Monitoring of Predict Decompensated Heart Failure", Am J Cardiol, vol. 99 (4), 2007, pp. 554-557.

Yu, et al., "Intrathoracic Impedance Monitoring in Patients with Heart Failure: Correlation with Fluid Status and Feasibility of Early Warning Preceding Hospitalization", Circulation, vol. 112, 2005, pp. 841-848.

Zannad, et al., "Incidence, clinical and etiologic features, and outcomes of advanced chronic heart failure: The EPICAL Study", J Am Coll Cardiol, vol. 33 (3), 1999, pp. 734-742.

Zile, "Heart failure with preserved ejection fraction: is this diastolic heart failure?", J Am Coll Cardiol., vol. 41 (9), 2003, pp. 1519-1522.

Cleland, et al., "The EuroHeart Failure survey programme—a survey on the quality of care among patients with heart failure in Europe—Part 1: patient characteristics and diagnosis", European Heart Journal, vol. 24 (5), 2003, pp. 442-463.

Cooley, "The Parameters of Transthoracic Electrical Conduction", Annals of the New York Academy of Sciences, vol. 170 (2), 1970, pp. 702-713.

Cowie, et al., "Hospitalization of patients with heart failure. A population-based study", European Heart Journal, vol. 23 (11), 2002, pp. 877-885.

Dimri, "Chapter 1: Fractals in geophysics and semiology: an introduction", Fractal Behaviour of the Earth System, Springer Berlin Heidelberg, 2005, pp. 1-22.

(56) References Cited

OTHER PUBLICATIONS

El-Dawlatly, et al., "Impedance cardiography: noninvasive assessment of hemodynamics and thoracic fluid content during bariatric surgery", Obesity Surgery, vol. 15 (5), May 2005, pp. 655-658.
EM Microelectronic, "Plastic Flexible LCD", Product Brochure, retrieved from http://www.emmicroelectronic.com/Line.asp?IdLine=48, 2009, 2 pages.
Erdmann, "Editorials: The value of diuretics in chronic heart failure demonstrated by an implanted hemodynamic monitor", European Heart Journal, vol. 23 (1), 2002, pp. 7-9.
FDA—Medtronic Inc., "Chronicle 9520B Implantable Hemodynamic Monitor Reference Manual", 2007, 112 pages.
Flach, "U.S. Appl. No. 60/006,600, filed Nov. 13, 1995".
Fonarow, "How well are chronic heart failure patients being managed", Rev Cardiovasc Med., vol. 7 Suppl 1, 2006, pp. S3-S11.
Fonarow, "Maximizing Heart Failure Care", PowerPoint Presentation, downloaded from http://www.medreviews.com/media/MaxHFCore.ppt, date unknown, 130 pages.
Fonarow, "Proactive monitoring and management of the chronic heart failure patient", Rev Cardiovasc Med., vol. 7 Suppl 1, 2006, pp. S1-S2.
Fonarow, et al., "Risk stratification for in-hospital mortality in acutely decompensated heart failure: classification and regression tree analysis", JAMA, vol. 293 (5), Feb. 2, 2005, pp. 572-580.
Fonarow, "The Acute Decompensated Heart Failure National Registry (ADHERE): opportunities to improve care of patients hospitalized with acute decompensated heart failure", Rev Cardiovasc Med., vol. 4 Suppl 7, 2003, pp. S21-S30.
Ganion, et al., "Intrathoracic impedance to monitor heart failure status: a comparison of two methods in a chronic heart failure dog model", Congest Heart Fail., vol. 11 (4), 2005, pp. 177-181, 211.
Gass, et al., "Critical pathways in the management of acute decompensated heart failure: A CME-Accredited monograph", Mount Sinai School of Medicine, 2004, 32 pages.
Gheorghiade, et al., "Congestion is an important diagnostic and therapeutic target in heart failure", Rev Cardiovasc Med., vol. 7 Suppl 1, 2006, pp. 12-24.
Gilliam, III, et al., "Changes in heart rate variability, quality of life, and activity in cardiac resynchronization therapy patients: results of the HF-HRV registry", Pacing and Clinical Electrophysiology, vol. 30 (1), Jan. 18, 2007, pp. 56-64.
Gilliam, III, et al., "Prognostic value of heart rate variability footprint and standard deviation of average 5-minute intrinsic R-R intervals for mortality in cardiac resynchronization therapy patients", J Electrocardiol., vol. 40 (4), Oct. 2007, pp. 336-342.
Gniadecka, et al., "Localization of dermal edema in lipodermatosclerosis, lymphedema, and cardiac insufficiency high-frequency ultrasound examination of intradermal echogenicity", J Am Acad oDermatol, vol. 35 (1), Jul. 1996, pp. 37-41.
Goldberg, et al., "Randomized trial of a daily electronic home monitoring system in patients with advanced heart failure: The Weight Monitoring in Heart Failure (WHARF) Trial", American Heart Journal, vol. 416 (4), Oct. 2003, pp. 705-712.
Grap, et al., "Actigraphy in the Critically Ill: Correlation with Activity, Agitation, and Sedation", American Journal of Critical Care, vol. 14, 2005, pp. 52-60.
Gudivaka, et al., "Single and multifrequency models for bioelectrical impedance analysis of body water compartments", J Appl Physiol, vol. 87 (3), 1999, pp. 1087-1096.
Guyton, et al., "Unit V: The Body Fluids and Kidneys, Chapter 25: The Body Fluid Compartments: Extracellular and Intracellular Fluids; Interstitial Fluid and Edema", Guyton and Hall Textbook of Medical Physiology 11th Edition, Saunders, 2005, pp. 291-306.
Hadase, et al., "Very low frequency power of heart rate variability is a powerful predictor of clinical prognosis in patients with congestive heart failure", Circ J., vol. 68 (4), 2004, pp. 343-347.
Hallstrom, et al., "Structural relationships between measures based on heart beat intervals: potential for improved risk assessment", IEEE Biomedical Engineering, vol. 51 (8), 2004, pp. 1414-1420.

HRV Enterprises LLC, "Heart Rate Variability Seminars", downloaded from http://hrventerprise.com, downloaded Apr. 24, 2008, 3 pages.
HRV Enterprises LLC, "LoggerPro HRV Biosignal Analysis", downloaded from http://hrventerprise.com/products.html, downloaded Apr. 24, 2008, 3 pages.
Hunt, et al., "ACC/AHA Guideline Update for the Diagnosis and Management of Chronic Heart Failure in the Adult: A Report of the American College of Cardiology/American Heart Association Task Force on Practice Guidelines:", Developed in Collaboration with the American College of Chest Physicians and the International Society for Heart and Lung Transplantation: Endorsed by the Heart Rhythm Society, Circulation, vol. 112, 2005, E154-E235.
Hunt, et al., "ACC/AHA Guidelines for the Evaluation and Management of Chronic Heart Failure in the Adult: Executive Summary A Report of the American College of Cardiology/American Heart Association Task Force on Practice Guidelines", Circulation, vol. 104, 2001, pp. 2996-3007.
Imhoff, et al., "Noninvasive whole-body electrical bioimpedance cardiac output and invasive thermodilution cardiac output in high-risk surgical patients", Critical Care Medicine, vol. 28 (8), 2000, pp. 21812-22818.
Jaeger, et al., "Evidence for Increased Intrathoracic Fluid Volume in Man at High Altitude", J Appl Physiol., vol. 47 (6), 1979, pp. 670-676.
Jaio, et al., "Variance fractal dimension analysis of seismic refraction signals", WESCANEX 97: Communications, Power and Computing, IEEE Conference Proceedings, May 22-23, 1997, pp. 163-167.
Jerant, et al., "Reducing the cost of frequent hospital admissions for congestive heart failure: a randomized trial of a home telecare intervention", Medical Care, vol. 39 (11), 2001, pp. 1234-1245.
Kasper, et al., "A randomized trial of the efficacy of multidisciplinary care in heart failure outpatients at high risk of hospital readmission", J Am Coll Cardiol, vol. 39, 2002, pp. 471-480.
Kaukinen, "Cardiac output measurement after coronary artery bypass grafting using bolus thermodilution, continuous thermodilution, and whole-body impedance cardiography", Journal of Cardiothoracic and Vascular Anesthesia, vol. 17 (2), 2003, pp. 199-203.
Kawaguchi, et al., "Combined ventricular systolic and arterial stiffening in patients with heart failure and preserved ejection fraction: implications for systolic and diastolic reserve limitations", Circulation, vol. 107, 2003, pp. 714-720.
Kawasaki, et al., "Heart rate turbulence and clinical prognosis in hypertrophic cardiomyopathy and myocardial infarction", Circ J., vol. 67 (7), 2003, pp. 601-604.
Kearney, et al., "Predicting death due to progressive heart failure in patients with mild-to-moderate chronic heart failure", J Am Coll Cardiol, vol. 40 (10), 2002, pp. 1801-1808.
Kitzman, et al., "Pathophysiological characterization of isolated diastolic heart failure in comparison to systolic heart failure", JAMA, vol. 288 (17), Nov. 2002, pp. 2144-2150.
Koobi, et al., "Non-invasive measurement of cardiac output: whole-body impedance cardiography in simultaneous comparison with thermodilution and direct oxygen Fick methods", Intensive Care Medicine, vol. 23 (11), 1997, pp. 1132-1137.
Koyama, et al., "Evaluation of heart-rate turbulence as a new prognostic marker in patients with chronic heart failure", Circ J, vol. 66 (10), 2002, pp. 902-907.
Kristofer, et al., "U.S. Appl. No. 60/972,336", filed Sep. 14, 2007.
Kristofer, et al., "U.S. Appl. No. 60/972,340", filed Sep. 14, 2007.
Kristofer, et al., "U.S. Appl. No. 60/972,343", filed Sep. 14, 2007.
Krumholz, et al., "Predictors of readmission among elderly survivors of admission with heart failure", American Heart Journal, vol. 139 (1), 2000, pp. 72-77.
Kyle, et al., "Bioelectrical Impedance Analysis—part I: review of principles and methods", Clin Nutr., vol. 23 (5), Oct. 2004, pp. 1226-1243.
Kyle, et al., "Bioelectrical Impedance Analysis—part II: utilization in clinical practice", Clin Nutr., vol. 23 (5), Oct. 2004, pp. 1430-1453.
Landrum, "U.S. Appl. No. 61/079,746", filed Jul. 10, 2008.

(56) References Cited

OTHER PUBLICATIONS

Lee, et al., "Predicting mortality among patients hospitalized for heart failure: derivation and validation of a clinical model", JAMA, vol. 290 (19), 2003, pp. 2581-2587.
ADVAMED White Sheet, "Health Information Technology: Improving Patient Safety and Quality of Card" Jun. 2005, 23 pages.
"Acute Decompensated Heart Failure", Wikipedia Entry, downloaded from: http://en.wikipedia.org/wiki/Acute_decompensated_heart_failure, downloaded Feb. 11, 2011, 6 pages.
"AD5934: 250kSPS 12-Bit Impedance Converter Network Analyzer, Analog Devices", retrieved from http://www.analog.com/static/imported-files/data_sheets/AD5934.pdf, date unknown, 40 pages.
"FDA—Draft questions for Chronicle Advisory Panel Meeting", retrieved from http://www.fda.gov/ohrms/dockets/ac/07/questions/2007-4284q1_draft.pdf, 2007, 3 pages.
"FDA—Medtronic Chronicle Implantable Hemodynamic Monitoring System P050032", Panel Package Section 11: Chronicle IHM Summary of Safety and Effectiveness, 2007, 77 pages.
"FDA—References for Circulatory System Devices Panel", retrieved from http://www.fda.gov/OHRMS/DOCKETS/AC/07/briefing/2007-4284bib1_01.pdf, Mar. 1, 2007, 1 page.
"FDA Executive Summary Memorandum, meeting of the Circulatory Systems Devices Advisory Panel", P050032 Medtronic, Inc. Chronicle Implantable Hemodynamic Monitor (IHM) System, retrieved from http://www.fda.gov.ohrms/dockets/ac/07/briefing/2007-4284b1_02.pdf, Mar. 1, 2007, 23 pages.
"FDA Executive Summary, Medtronic Chronicle Implantable Hemodynamic Monitoring System P050032: Executive Summary", Panel Package Sponsor Executive Summary, vol. 1, Sec. 4, retrieved from http://www.fda.gov/OHRMS/DOCKETS/AC/07/briefing/2007-4284b1_03.pdf, 2007, 12 pages.
"FDA Panel Recommendation", Chronicle Analysis, Mar. 1, 2007, 14 pages.
"Heart Failure", Wikipedia Entry, downloaded from http://en.wikipedia.org/wiki/Heart_failure, downloaded Feb. 11, 2011, 17 pages.
"HFSA Comprehensive Heart Failure Practice Guideline—Executive Summary: HFSA Comprehensive Heart Failure Practice Guideline", Journal of Cardiac Failure, vol. 12 (1), 2006, pp. 10-e38.
"HFSA Comprehensive Heart Failure Practice Guideline—Section 12: Evaluation and Management of Patients with Acute Decompensated Heart Failure", Journal of Cardiac Failure, vol. 12 (1), 2006, pp. E86-E103.
"HFSA Comprehensive Heart Failure Practice Guideline—Section 2: Conceptualization and Working Definition of Heart Failure", Journal of Cardiac Failure, vol. 12 (1), 2006, pp. E10-E11.
"HFSA Comprehensive Heart Failure Practice Guideline—Section 4: Evaluation of Patients for Ventricular Dysfunction and Heart Failure", Journal of Cardiac Failure, vol. 12 (1), 2006, pp. E16-E25.
"HFSA Comprehensive Heart Failure Practice Guideline—Section 8: Disease Management in Heart Failure Education and Counseling", Journal of Cardiac Failure, vol. 12 (1), 2006, pp. E58-E68.
"HFSA Comprehensive Heart Failure Practice Guideline—Section 3: Prevention of Ventricular Remodeling Cardiac Dysfunction, and Heart Failure Overview", Journal of Cardiac Failure, vol. 12 (1), 2006, pp. E12-E15.
"LifeShirt Model 200 Directions for Use, Introduction", VivoMetrics, Inc., date unknown, 9 pages.
3M Corporation, "3M Surgical Tapes—Choose the Correct Tape", quicksheet, 2004.
Abraham, "New approaches to monitoring heart failure before symptoms appear", Rev. Cardiovasc. Med., vol. 7 Suppl 1, 2006, pp. 33-41.
Adams, Jr., "Guiding heart failure care by invasive hemodynamic measurements: possible or useful?", Journal of Cardiac Failure, vol. 8 (2), 2002, pp. 71-73.
Adamson, et al., "Continuous autonomic assessment in patients with symptomatic heart failure: prognostic value of heart rate variability measured by an implanted cardiac resynchronization device", Circulation, vol. 110, 2004, pp. 2389-2394.
Adamson, "Integrating device monitoring into the infrastructure and workflow of routine practice", Rev. Cardiovasc. Med., vol. 7 Suppl 1, 2006, pp. 42-60.
Adamson, et al., "Ongoing right ventricular hemodynamics in heart failure", J. Am. Coll. Cardiol, vol. 41, 2003, pp. 565-570.
Adhere, "Insights from the Adhere Registry: Data from over 1,000,000 patient cases", Presentation, date unknown, 70 pages.
Advamed, "Health Information Technology: Improving Patient Safety and Quality of Care", Jun. 2005, 23 pages.
Aghababian, "Acutely decompensated heart failure: opportunities to improve care and outcomes in the emergency department", Rev. Cardiovasc. Med., vol. 3 Suppl 4, 2002, pp. S3-S9.
Albert, "Bioimpedance to prevent heart failure hospitalization", Curr Heart Fail Rep., vol. 3 (3), Sep. 2006, pp. 136-142.
American Heart Association, "Heart Disease and Stroke Statistics—2006 Update", 2006, 43 pages.
American Heart Association, "Heart Disease and Stroke Statistics—2007 Update", A Report from the American Heart Association Statistics Committee and Stroke Statistics Subcommittee; Circulation, 115, 2007, pp. e69-e171.
Amurthur, et al., "U.S. Appl. No. 60/972,359", filed Sep. 14, 2007.
Amurthur, et al., "U.S. Appl. No. 60/972,363", filed Sep. 14, 2007.
Belalcazar, et al., "Monitoring lung edema using the pacemaker pulse and skin electrodes", Physiol. Meas., vol. 26, 2005, pp. S153-S163.
Bennett, "Development of implantable devices for continuous ambulatory monitoring of central hemodynamic values in heart failure patients", PACE, vol. 28, Jun. 2005, pp. 573-584.
Bly, et al., "U.S. Appl. No. 60/972,333", filed Sep. 14, 2007.
Bly, et al., "U.S. Appl. No. 60/972,629", filed Sep. 14, 2007.
Bly, et al., "U.S. Appl. No. 61/055,645", filed May 23, 2008.
Bly, "U.S. Appl. No. 61/084,567", filed Jul. 29, 2008.
Bourge, "Case studies in advanced monitoring with the chronicle device", Rev Cardiovasc Med., vol. 7 Suppl 1, 2006, pp. S56-S61.
Braunschweig, "Continuous hemodynamic monitoring during withdrawal of diuretics in patients with congestive heart failure", European Heart Journal, vol. 23 (1), 2002, pp. 59-69.
Braunschweig, "Dynamic changes in right ventricular pressures during hemodialysis recorded with an implantable hemodynamic monitor", Nephrol Dial Transplant, vol. 21, 2006, pp. 176-183.
Brennan, "Measuring a Grounded Impedance Profile Using the AD5933", Analog Devices, retrieved from http://www.analog.com/static/imported-files/application_notes/427095282381510189AN847_0.pdf, date unknown, 12 pages.
Buono, et al., "The effect of ambient air temperature on whole-body bioelectrical impedance", Physiol. Meas., vol. 25, 2004, pp. 119-123.
Burkhoff, et al., "Heart failure with a normal ejection fraction: Is it really a disorder of diastolic function?", Circulation, vol. 107, 2003, pp. 656-658.
Burr, et al., "Heart rate variability and 24-hour minimum heart rate", Biological Research for Nursing, vol. 7 (4), 2006, pp. 256-267.
Cardionet, "CardioNet Mobile Cardiac Outpatient Telemetry: Addendum to Patient Education Guide", CardioNet, Inc., 2007, 2 pages.
Cardionet, "Patient Education Guide", CardioNet, Inc., 2007, 7 pages.
Charach, et al., "Transthoracic monitoring of the impedance of the right lung in patients with cardiogenic pulmonary edema", Crit Care Med, vol. 29 (6), 2001, pp. 1137-1144.
Charlson, et al., "Can disease management target patients most likely to generate high costs? The Impact of Comorbidity", Journal of General Internal Medicine, vol. 22 (4), 2007, pp. 464-469.
Chaudhry, et al., "Telemonitoring for patients with chronic heart failure: a systematic review", J Card Fail., vol. 13 (1), Feb. 2007, pp. 56-62.
Chung, et al., "White coat hypertension: Not so benign after all?", Journal of Human Hypertension, vol. 17, 2003, pp. 807-809.
Leier, "The Physical Examination in Heart Failure—Part I", Congest Hear Fail., vol. 13 (1), Jan.-Feb. 2007, pp. 41-47.
Libbus, et al., "U.S. Appl. No. 60/972,316", filed Sep. 12, 2008.
Libbus, et al., "U.S. Appl. No. 60/972,512", filed Sep. 14, 2007.

(56) References Cited

OTHER PUBLICATIONS

Libbus, et al., "U.S. Appl. No. 60/972,581", filed Sep. 14, 2007.
Libbus, et al., "U.S. Appl. No. 60/972,616", filed Sep. 14, 2007.
Libbus, et al., "U.S. Appl. No. 61/035,970", filed Mar. 12, 2008.
Libbus, et al., "U.S. Appl. No. 61/047,875", filed Apr. 25, 2008.
Libbus, et al., "U.S. Appl. No. 61/055,656", filed May 23, 2008.
Liu, et al., "Fractal analysis with applications to seismological pattern recognition of underground nuclear explosions", Signal Processing, vol. 80 (9), Sep. 2000, pp. 1849-1861.
Lozano-Nieto, "Impedance ratio in bioelectrical impedance measurements for body fluid shift determination", Proceedings of the IEEE 24th Annual Northeast Bioengineering Conference, Apr. 9-10, 1998, pp. 24-25.
Lucreziotti, et al., "Five-minute recording of heart rate variability in severe chronic heart failure: Correlates with right ventricular function and prognostic implications", American Heart Journal, vol. 139 (6), 2000, pp. 1088-1095.
Luthje, et al., "Detection of heart failure decompensation using intrathoracic impedance monitoring by a triple-chamber implantable defibrillator", Heart Rhythm, vol. 2 (9), Sep. 2005, pp. 997-999.
Magalski, et al., "Continuous ambulatory right heart pressure measurements with an implantable hemodynamic monitor: a multicenter, 12-Month Follow-Up Study of Patients with Chronic Heart Failure", J Card Fail, vol. 8 (2), 2002, pp. 63-70.
Mahlberg, et al., "Actigraphy in agitated patients with dementia: Monitoring treatment outcomes", Zeitschrift fur Gerontologie und Geriatrie, vol. 40 (3), Jun. 2007, pp. 178-184.
Manicka, et al., "U.S. Appl. No. 60/972,329", filed Sep. 14, 2007.
Manicka, et al., "U.S. Appl. No. 60/972,537", filed Sep. 14, 2007.
Manicka, et al., "U.S. Appl. No. 61/055,666", filed May 23, 2008.
Matthie, et al., "Analytic assessment of the various bioimpedance methods used to estimate body water", Appl Physiol, vol. 84 (5), 1998, pp. 1801-1816.
Matthie, et al., "Second generation mixture theory equation for estimating intracellular water using bioimpedance spectroscopy", J Appl Physiol, vol. 99, 2005, pp. 780-781.
Mazar, et al., "U.S. Appl. No. 60/972,354", filed Sep. 14, 2007.
Mazar, "U.S. Appl. No. 61/046,196", filed Apr. 18, 2008.
McMurray, et al., "Heart Failure: Epidemiology, Aetiology, and Prognosis of Heart Failure", Heart, vol. 83, 2000, pp. 596-602.
Miiller, "Home monitoring for congestive heart failure patients", Caring Magazine, Aug. 1995, pp. 53-54.
Moser, et al., "Improving outcomes in heart failure: it's not unusual beyond usual Care", Circulation, vol. 105, 2002, pp. 2810-2812.
Nagels, et al., "Actigraphic measurement of agitated behaviour in dementia", International Journal of Geriatric Psychiatry, vol. 21 (4), 2009, pp. 388-393.
Nakamura, et al., "Universal scaling law in human behavioral organization", Physical Review Letters, vol. 99 (13), Sep. 28, 2007, 4 pages.
Nakaya, "Fractal properties of seismicity in regions affected by large, shallow earthquakes in western Japan: Implications for fault formation processes based on a binary fractal fracture network model", Journal of Geophysical Research, vol. 11 (B1), Jan. 2005, pp. B01310.1-B01310.15.
Naylor, et al., "Comprehensive discharge planning for the hospitalized elderly: a randomized clinical trial", Amer. College Physicians, vol. 120 (12), 1994, pp. 999-1006.
Nesiritide (Natrecor), "Acutely Decompensated Congestive Heart Failure: Burden of Disease", Presentation, downloaded from http://www.huntsvillehospital.org/foundation/events/cardiologyupdate/CHF.ppt, date unknown, 39 pages.

Nieminen, et al., "EuroHeart Failure Survey II (EHFSII): a survey on hospitalized acute heart failure patients: description of population", European Heart Journal, vol. 27 (22), 2006, pp. 2725-2736.
Nijsen, et al., "The potential value of three-dimensional accelerometry for detection of motor seizures in severe epilepsy", Epilepsy Behav., vol. 7 (1), Aug. 2005, pp. 74-84.
Noble, et al., "Diuretic induced change in lung water assessed by electrical impedance tomography", Physiol. Meas., vol. 21 (1), 2000, pp. 155-163.
Noble, et al., "Monitoring patients with left ventricular failure by electrical impedance tomography", Eur J Heart Fail., vol. 1 (4), Dec. 1999, pp. 379-384.
O'Connell, et al., "Economic impact of heart failure in the United States: time for a different approach", J Heart Lung Transplant., vol. 13 (4), Jul.-Aug. 1994, p. S107-S112.
Ohlsson, et al., "Central hemodynamic responses during serial exercise tests in heart failure patients using implantable hemodynamic monitors", Eur J Heart Fail., vol. 5 (3), Jun. 2003, pp. 253-259.
Ohlsson, et al., "Continuous ambulatory monitoring of absolute right ventricular pressure and mixed venous oxygen saturation in patients with heart failure using an implantable hemodynamic monitor", European Heart Journal, vol. 22 (11), 2001, pp. 942-954.
Packer, et al., "Utility of impedance cardiography for the identification of short-term risk of clinical decompensation in stable patients with chronic heart failure", J. Am. Coll Cardiol, vol. 47 (11), 2006, pp. 2245-2252.
Palatini, et al., "Predictive value of clinic and ambulatory heart rate for mortality in elderly subjects with systolic hypertension", Arch Intern Med., vol. 162, 2002, pp. 2313-2321.
PCT/US2008/076247, "International Search Report and Written Opinion", for International Patent Application PCT/ US2008/076247, filed Sep. 12, 2008.
Piiria, et al., "Crackles in patients with fibrosing alveolitis bronchiectasis, COPD, and Heart Failure", Chest, vol. 99 (5), May 1991, pp. 1076-1083.
Pocock, et al., "Predictors of mortality in patients with chronic heart failure", Eur Heart J, vol. 27, 2006, pp. 65-75.
Poole-Wilson, et al., "Importance of control of fluid volumes in heart failure", European Heart Journal,vol. 22 (11), 2000, pp. 893-894.
Raj, et al., "Letter Regarding Article by Adamson et al. Continuous Autonomic Assessment in Patients with Symptomatic Heart Failure: Prognostic Value of Heart Rate Variability Measured by an Implanted Cardiac Resynchronization Device", Circulation, vol. 112, 2005, pp. E37-E38.
Ramirez, et al., "Prognostic value of hemodynamic findings from impedance cardiography in hypertensive stroke", AJH, vol. 18 (20), 2005, pp. 65-72.
Rich, et al., "A multidisciplinary intervention to prevent the readmission of elderly patients with congestive heart failure", New Engl. J. Med., vol. 333, 1995, pp. 1190-1195.
Scharf, et al., "Direct digital capture of pulse oximetry waveforms", Proceedings of the Twelfth Southern Biomedical Engineering Conference, 1993, pp. 230-232.
Shabetai, "Monitoring heart failure hemodynamics with an implanted device: its potential to improve outcome", J Am Coll Cardiol, vol. 41, 2003, pp. 572-573.
Small, "Integrating monitoring into the infrastructure and workflow of routine practice: OptiVol", Rev Cardiovasc Med., vol. 7 Supp 1, 2006, pp. S47-S55.
Smith, et al., "Outcomes in heart failure patients with preserved ejection fraction: mortality, readmission, and functional decline", J Am Coll Cardiol, vol. 41, 2003, pp. 1510-1518.
Starling, "Improving care of chronic heart failure: advances from drugs to devices", Cleveland Clinic Journal of Medicine, vol. 70 (2), Feb. 2003, pp. 141-146.

\* cited by examiner

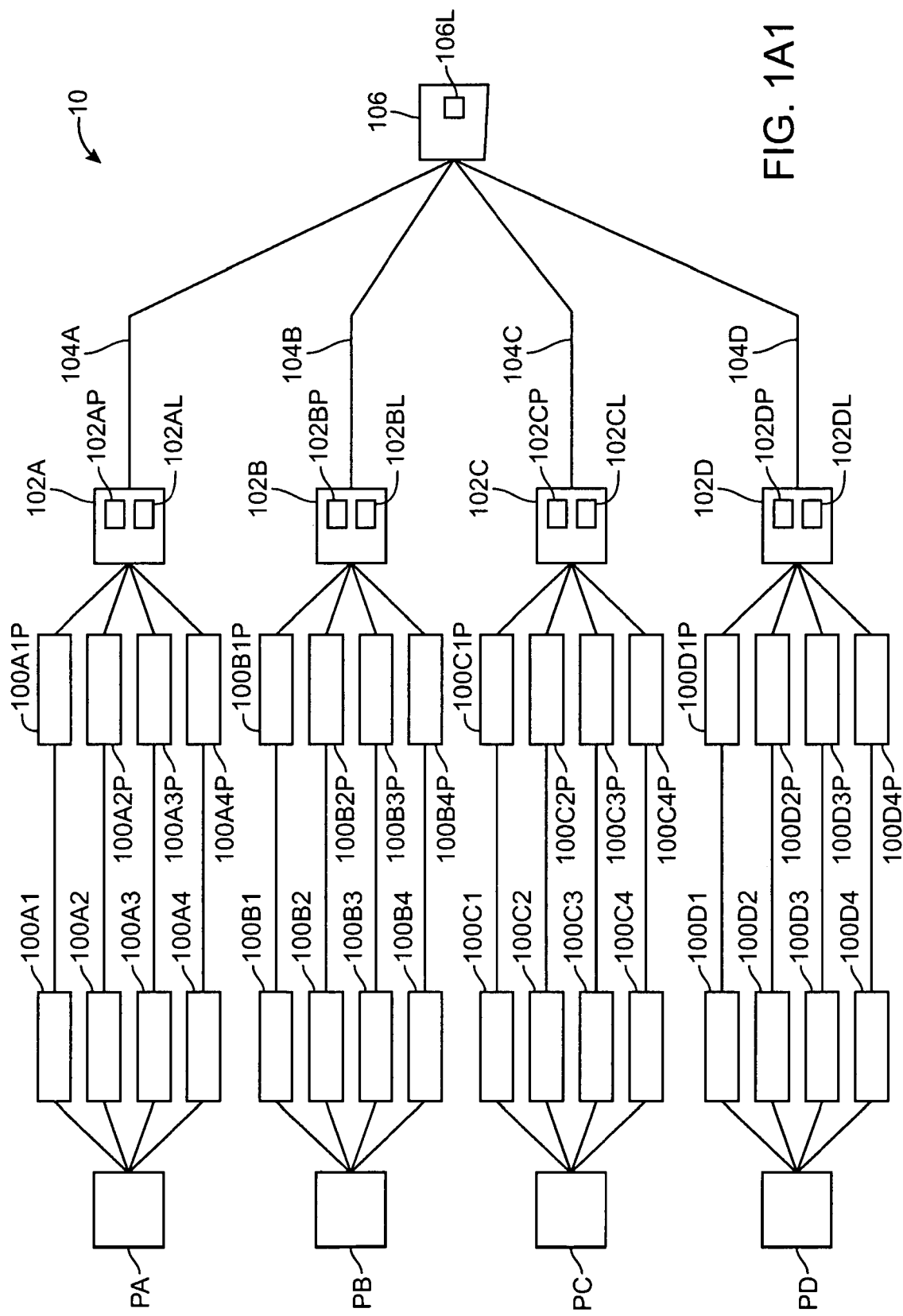
FIG. 1A1

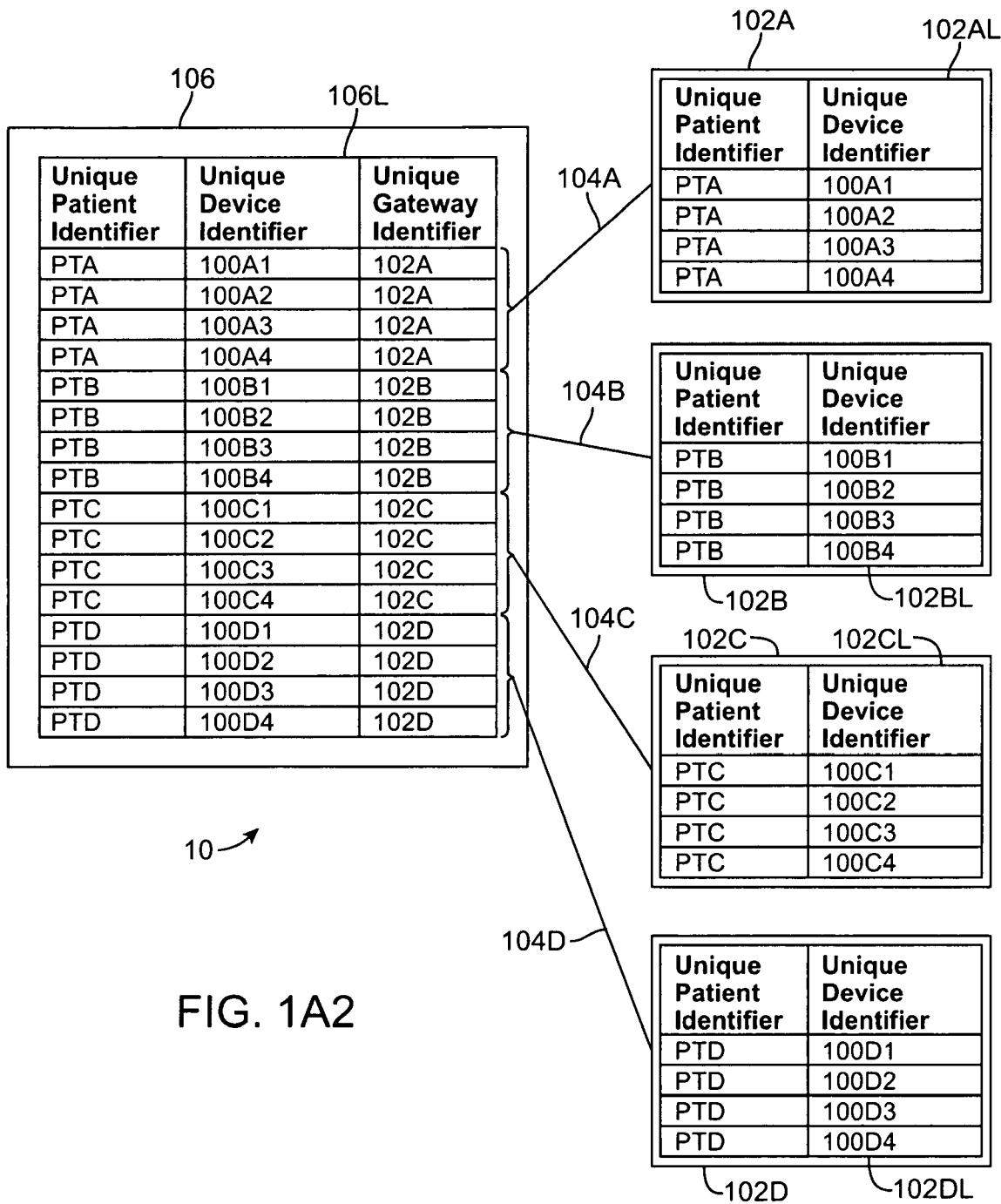
FIG. 1A2

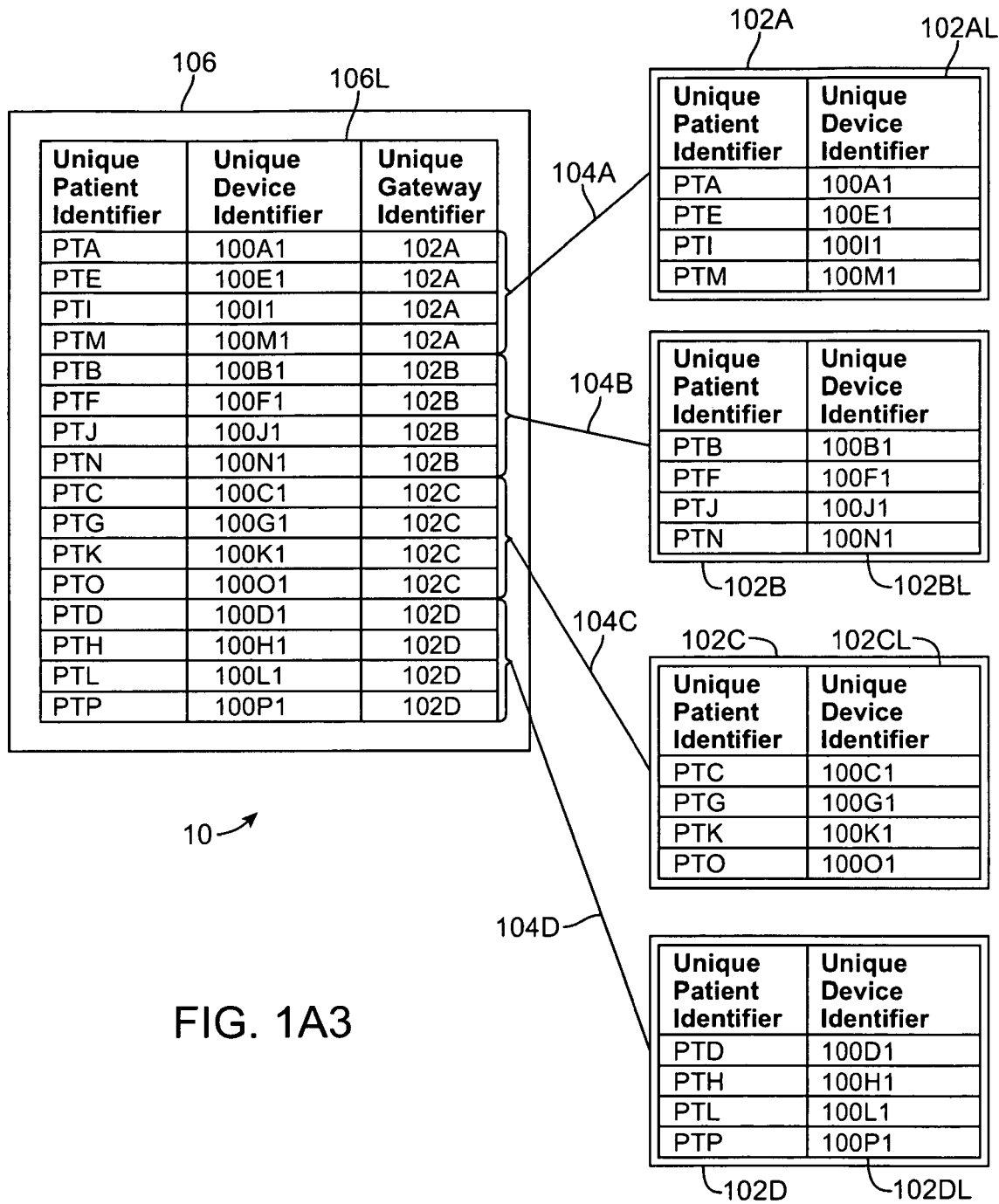
FIG. 1A3

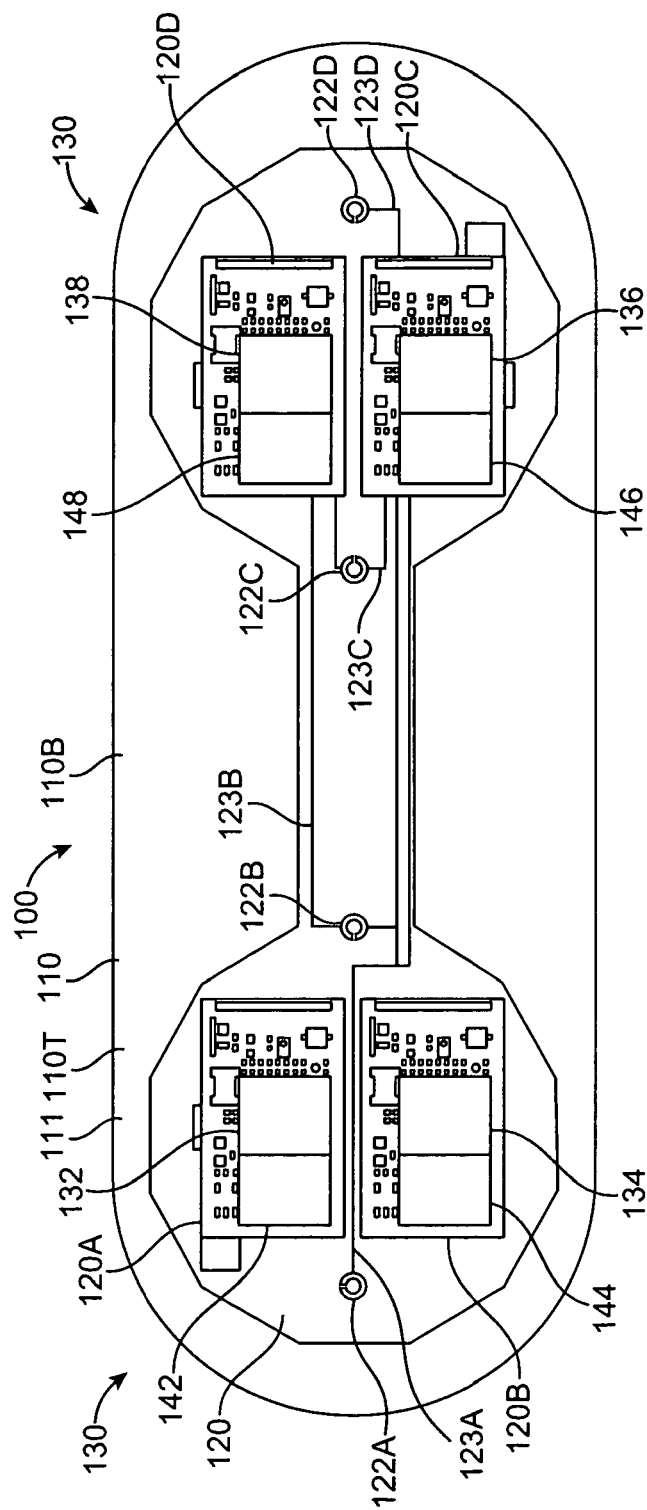
FIG. 1D
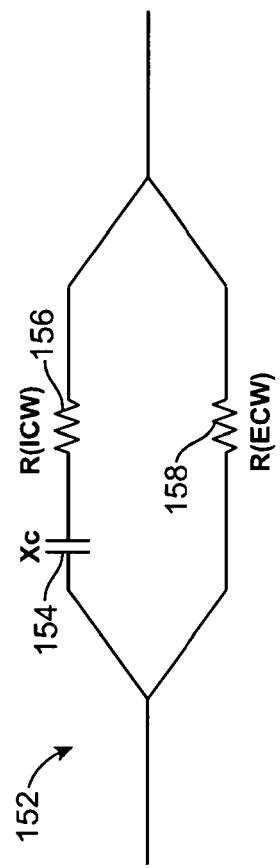
FIG. 1D1

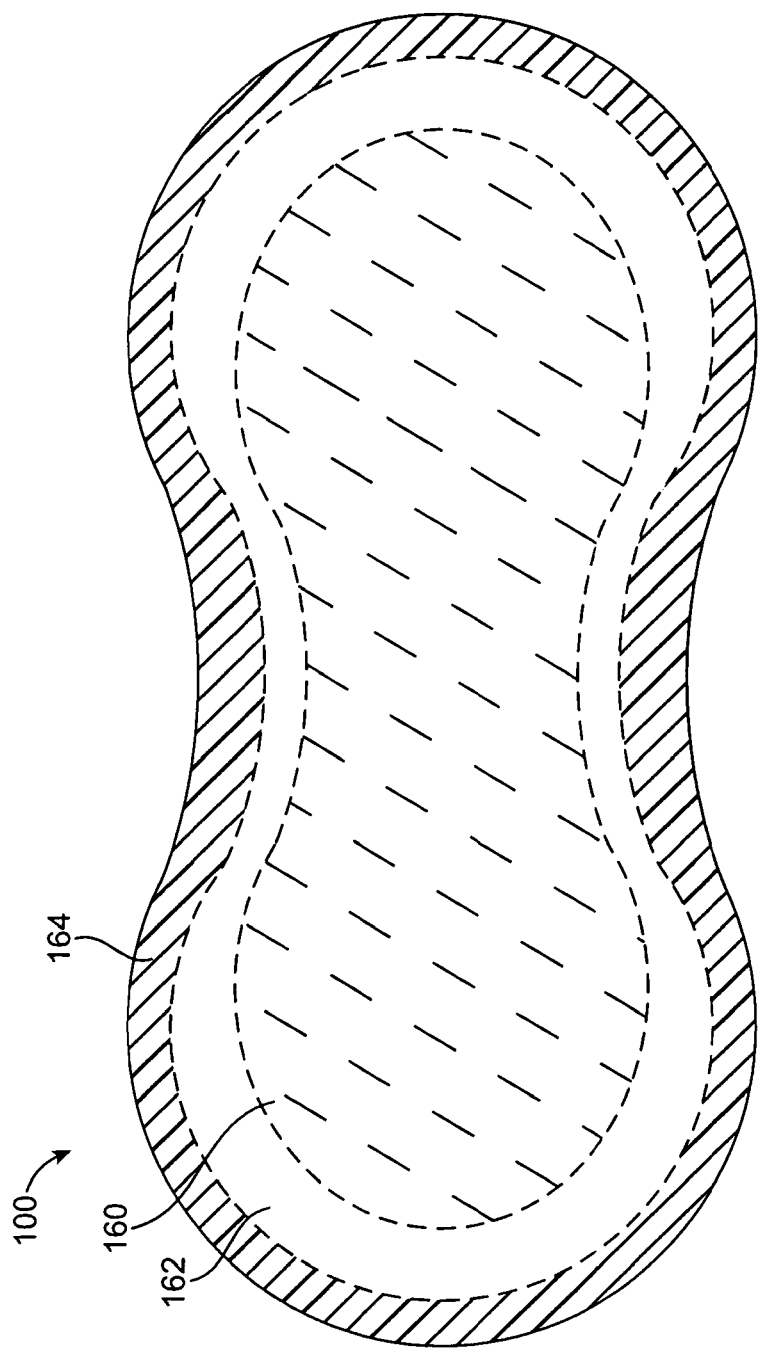

DYNAMIC PAIRING OF PATIENTS TO DATA COLLECTION GATEWAYS

CROSS-REFERENCES TO RELATED APPLICATIONS

The present application is a divisional of U.S. application Ser. No. 12/209,278 filed on Sep. 12, 2008, now U.S. Pat. No. 9,411,936, which claims benefit under 35 USC 119(e) of U.S. Provisional Application Nos. 60/972,537, 60/972,340, and 60/972,336 all filed Sep. 14, 2007, 61/055,666 filed May 23, 2008, and 61/079,746 filed Jul. 10, 2008. The full disclosures of these applications are incorporated herein by reference in their entirety.

The subject matter of the present application is related to the following applications: 60/972,512; 60/972,329; 60/972,354; 60/972,616; 60/972,363; 60/972,343; 60/972,581; 60/972,629; 60/972,316; 60/972,333; 60/972,359 all of which were filed on Sep. 14, 2007; 61/046,196 filed Apr. 18, 2008; 61/047,875 filed Apr. 25, 2008; and 61/055,645, 61/055,656, 61/055,662, 61/055,666 all filed May 23, 2008.

The following applications are being filed concurrently with the present application, on Sep. 12, 2008: U.S. application Ser. No. 12/209,279 entitled "Multi-Sensor Patient Monitor to Detect Impending Cardiac Decompensation Prediction"; U.S. application Ser. No. 12/209,288 entitled "Adherent Device with Multiple Physiological Sensors"; U.S. application Ser. No. 12/209,430 entitled "Injectable Device for Physiological Monitoring"; U.S. application Ser. No. 12/209,479 entitled "Delivery System for Injectable Physiological Monitoring System"; U.S. application Ser. No. 12/209,262 entitled "Adherent Device for Cardiac Rhythm Management"; U.S. application Ser. No. 12/209,268 entitled "Adherent Device for Respiratory Monitoring"; U.S. application Ser. No. 12/209,269 entitled "Adherent Athletic Monitor"; U.S. application Ser. No. 12/209,259 entitled "Adherent Emergency Monitor"; U.S. application Ser. No. 12/209,273 entitled "Adherent Device with Physiological Sensors"; U.S. application Ser. No. 12/209,276 entitled "Medical Device Automatic Start-up upon Contact to Patient Tissue"; U.S. application Ser. No. 12/210,078 entitled "System and Methods for Wireless Body Fluid Monitoring"; U.S. application Ser. No. 12/209,265 entitled "Adherent Cardiac Monitor with Advanced Sensing Capabilities"; U.S. application Ser. No. 12/209,292 entitled "Adherent Device for Sleep Disordered Breathing"; U.S. application Ser. No. 12/209,508 entitled "Adherent Multi-Sensor Device with Implantable Device Communications Capabilities"; U.S. application Ser. No. 12/209,528 entitled "Data Collection in a Multi-Sensor Patient Monitor"; U.S. application Ser. No. 12/209,271 entitled "Adherent Multi-Sensor Device with Empathic Monitoring"; U.S. application Ser. No. 12/209,274 entitled "Energy Management for Adherent Patient Monitor"; and U.S. application Ser. No. 12/209,294 entitled "Tracking and Security for Adherent Patient Monitor."

BACKGROUND OF THE INVENTION

1. Field of the Invention

The present invention relates to patient monitoring and therapy. Although embodiments make specific reference to monitoring impedance and electrocardiogram signals with an adherent patch, the system methods and device described herein may be applicable to many applications in which physiological monitoring is used, for example wireless physiological monitoring for extended periods.

Patients are often treated for diseases and/or conditions associated with a compromised status of the patient, for example a compromised physiologic status. In some instances, a patient may report symptoms that require diagnosis to determine the underlying cause. For example, a patient may report fainting or dizziness that requires diagnosis, in which long term monitoring of the patient can provide useful information as to the physiologic status of the patient. In some instances, a patient may have suffered a heart attack and require care and/or monitoring after release from the hospital. One example of a device to provide long term monitoring of a patient is the Holter monitor, or ambulatory electrocardiography device. In addition to measuring heart signals with electrocardiograms, known physiologic can include many kinds of measurements, for example impedance measurements to measure hydration of the patient.

Work in relation to embodiments of the present invention suggests that known methods and apparatus for long term monitoring of patients may be less than ideal. At least some of the known devices may not be configured to transmit data optimally from a patient measurement device a patient monitoring center, for example from a wearable device to a backend server. For example, when several patients are monitored many wireless devices may be used. At least some of these devices may be allowed to communicate simultaneously through a single gateway device, such that communication through the gateway device may become slow, for example somewhat slower than ideal. In at least some instances, important information may not pass through the gateway to a remote site in a timely manner. In addition, at least some of the known communication schemes may not provide a well maintained path from the gateway to the remote site and/or backend server, such that communication from the gateway to the remote site and/or backend server can be further delayed in some instances. Some of the known systems for patient monitoring can be expensive and/or cumbersome to use, such that at least some patients may be deprived of the potential benefit of extended monitoring such as at home monitoring.

Some of the known communication systems may be less than ideal for patient monitoring. Although some known wireless devices can permit pairing, at least some of these known pairing schemes may not provide sufficient flexibility and ease of use for patient monitoring. Known pairing schemes, for example Bluetooth connections for cellular phones, can be somewhat cumbersome and may not be well suited for patient monitoring in at least some instances. Although hard wiring may facilitate paring with some devices in some instances, hardwiring may result in less flexibility and may not be well suited for patient monitoring, for example when a device paired with hard wiring is replaced with another hard wired device.

Therefore, a need exists for improved patient monitoring. Ideally, such improved patient monitoring would avoid at least some of the short-comings of the present methods and devices.

2. Description of the Background Art

The following U.S. Patents and Publications may describe relevant background art: U.S. Pat. Nos. 4,121,573; 4,955,381; 4,981,139; 5,080,099; 5,353,793; 5,511,553; 5,544,661; 5,558,638; 5,724,025; 5,772,586; 5,862,802; 5,944,659; 6,047,203; 6,117,077; 6,129,744; 6,225,901; 6,385,473; 6,416,471; 6,454,707; 6,527,711; 6,527,729; 6,551,252; 6,595,927; 6,595,929; 6,605,038; 6,645,153; 6,659,947; 6,821,249; 6,980,851; 6,988,989; 7,020,508; 7,054,679; 7,130,396; 7,153,262; 2003/0092975; 2004/0225199;

2005/0113703; 2005/0131288; 2006/0010090; 2006/0031102; 2006/0074462; 2006/0089679; 2006/0122474; 2006/0142820; 2006/0155183; 2006/0202816; 2006/0224051; 2006/0235281; 2006/0264730; 2007/0015973; 2007/0180047; 2007/0038038; and 2007/0021678.

BRIEF SUMMARY OF THE INVENTION

Embodiments of the present invention provide improved systems, devices and methods to transmit data from a patient device to a location, for example a remote location, where the patient is monitored. The system may comprise a server system, for example a backend server system, a gateway and a patient device, for example a patient worn device to collect patient data. The gateway can be configured to communicate with the patient worn device in response to a list transmitted from the server, for example an approved patient device list transmitted from the server to the gateway. In some embodiments, the gateway may exclude communication with patient worn devices that are not on the list. For example, the list may limit the number of patient worn devices that can communicate with each gateway. The transmitted list received at each gateway can control data transmitted from the patient device to the gateway and also data transmitted from the gateway to the server, such that the communication from the device on the list to the server is maintained and appropriate information can be reliably sent from the patient device to the server. This reliability of the communication from that patient worn device to the server can be especially important for treating a patient with a health condition, for example when the data transmitted comprises cardiac data that can be used to save the patient's life. The system may comprise a plurality of patient worn devices and a plurality of gateways, each configured to transmit data to a backend server. The system can transmit data reliably when there are many patches and patients configured to transmit data on the system, such that many people can benefit from monitoring. For example the plurality of patient worn devices may comprise at least about 10 patient worn devices, for example 100 or more patient worn devices, and a plurality of gateways, for example at least about 5 gateways, for example 50 or more gateways.

In a first aspect, embodiments of the present invention provide a system for monitoring a patient. The system comprises a server system. A patient device is coupled to the patient to measure patient data. The patient device comprises a communications module configured to transmit a device identifier. A gateway is configured to communicate with the server and the patient device. The gateway is configured to communicate with the patient device in response to the device identifier.

The patient device may comprise at least one of an adherent patient device, a wearable patient device, an implantable patient device, or an injectable patient device.

In many embodiments, the gateway is configured to pair with the patient device in response to the device identifier. The device identifier may comprise a unique device identifier. For example, the unique identifier may comprise a serial number of the patient device. The device identifier may comprise a link key to establish paired communication between the patient device and the gateway. At least one of the server system, the patient device or the gateway can be configured to determine an encryption key from the link key, and the patient device can be configured to encrypt the patient data for transmission with the encryption key.

In many embodiments, the patient device and the gateway are configured to communicate with paired communication in response to the device identifier. The gateway and the patient device can be configured to exchange a link key so as to pair the gateway with the patient device. For example, the gateway and the patient device may be configured to communicate with a communication protocol comprising at least one of a Zigbee protocol or a Bluetooth protocol.

In many embodiments, the gateway may comprise a list of device identifiers, and the list may comprise the device identifier. The list comprises a plurality of device identifiers, and each of the plurality of device identifiers may comprise a unique identifier specific to the patient device. For example, the list may comprise a range of identifiers and the device identifier can be within the range.

In many embodiments, the system comprises a plurality of patient devices, and the gateway is configured to pair with the plurality of patient devices, in which each patient device comprises a unique identifier. The gateway may be configured to pair simultaneously with the plurality of patient devices, and each device may be configured to transmit the unique identifier with patient data from the device.

In some embodiments, the gateway is configured to pair sequentially with the plurality of patient devices, and each device is configured to transmit the patient data when paired with the gateway.

In many embodiments, the server system comprises a list of allowable patient devices, in which the list comprises the device identifier, and the device identifier is transmitted from the server system to the gateway. The server system may comprise at least one processor comprising a tangible medium configured to receive patient data. For example, the server system comprises a plurality of processors.

In many embodiments, the patient device comprises at least one of an implantable device, a device worn by the patient or a device adhered to the patient.

In many embodiments, the server system comprises a backend server system at a site remote from the patient. The gateway and the server may be configured to communicate with at least a cellular connection, a dedicated connection or a prioritized internet connection.

In another aspect, embodiments of the present invention provide a system for monitoring a plurality of patients. The system comprises a plurality of patient devices. Each device is configured to couple to one of the plurality of patients to measure data from the patient, and each patient device comprises a unique patient device identifier. A server system comprises a tangible medium configured to store a list with the unique patient device identifier for each device. A plurality of gateways are configured communicate with the server system and the plurality of patient devices. Each gateway of the plurality of gateways is configured to communicate with at least one of the plurality of patient devices in response to the list.

In many embodiments, each gateway of the plurality of gateways is configured to exclude communication with each of the plurality of patient devices not identified on a gateway device list transmitted to the gateway.

In many embodiments, each gateway of the plurality of gateways comprises a unique gateway identifier. Each gateway of the plurality of gateways can be configured to communicate with at least one of the plurality of patient devices in response to the unique gateway identifier. For example, the unique gateway identifier for each gateway of the plurality of gateways may comprise a serial number.

In many embodiments, the server system comprises a tangible medium configured to transmit a gateway specific patient device list to each gateway. The gateway specific patient device list transmitted to each gateway may comprise a unique gateway specific patient device list transmitted in response to a unique gateway identifier. Each unique gateway specific patient device list may comprise at least one different unique patient device identifier. Each gateway of the plurality of gateways may be configured to exclude communication with each of the plurality of patient devices not identified on the gateway specific patient device list transmitted to the gateway. Each unique gateway specific patient device list may comprise separate unique patient device identifiers.

In many embodiments, each gateway of the plurality of gateways is configured to transmit the unique gateway identifier to the server with patient data and the unique patient device identifier.

In many embodiments, each gateway of the plurality of gateways comprises a gateway device list of allowed patient devices and is configured to communicate with each device identified on the gateway device list.

In many embodiments, each gateway is configured to transmit patient data and the unique patient device identifier from each patient device to the server system when the device is adhered to the patient.

In many embodiments, the plurality of gateways comprises at least about five gateways and the plurality of patient measurement devices comprises at least about ten patient measurement devices. Each gateway of the plurality of gateways can be configured to communicate with at least two patient devices, and each patient device may be allowed to communicate with no more than two gateways in response to the list.

In many embodiments, the list comprises at least one of a binary file, a hexadecimal file, an ASCII file or an encrypted file stored on the tangible medium of the server system. The server system may be configured to transmit at least a portion the list of unique patient device identifiers to the plurality of gateways.

BRIEF DESCRIPTION OF THE DRAWINGS

FIG. 1A1 shows the patient monitoring system of FIG. 1A with a plurality of gateways, each configured to transmit data in response to a list of allowed patient devices;

FIG. 1A2 shows a master approved patient device list and corresponding gateway approved patient device lists for the patient monitoring system of FIGS. 1A and 1A1;

FIG. 1A3 shows an updated master approved patient device list and corresponding updated gateway approved patient device lists for the patient monitoring system of FIGS. 1A, 1A1 and 1A2;

FIG. 1D shows a printed circuit boards and electronic components over the adherent patch, as in FIG. 1C;

FIG. 1D1 shows an equivalent circuit that can be used to determine optimal frequencies for determining patient hydration, according to embodiments of the present invention;

FIG. 1F shows a top view of an electronics housing and a breathable cover over the batteries, electronic components and printed circuit board as in FIG. 1E;

FIG. 2 shows a method of monitoring patient data including the transmission of data from a plurality of patient worn devices with a plurality of gateways in response to an approved device list, according to embodiments of the present invention.

DETAILED DESCRIPTION OF THE INVENTION

Figure 1A:
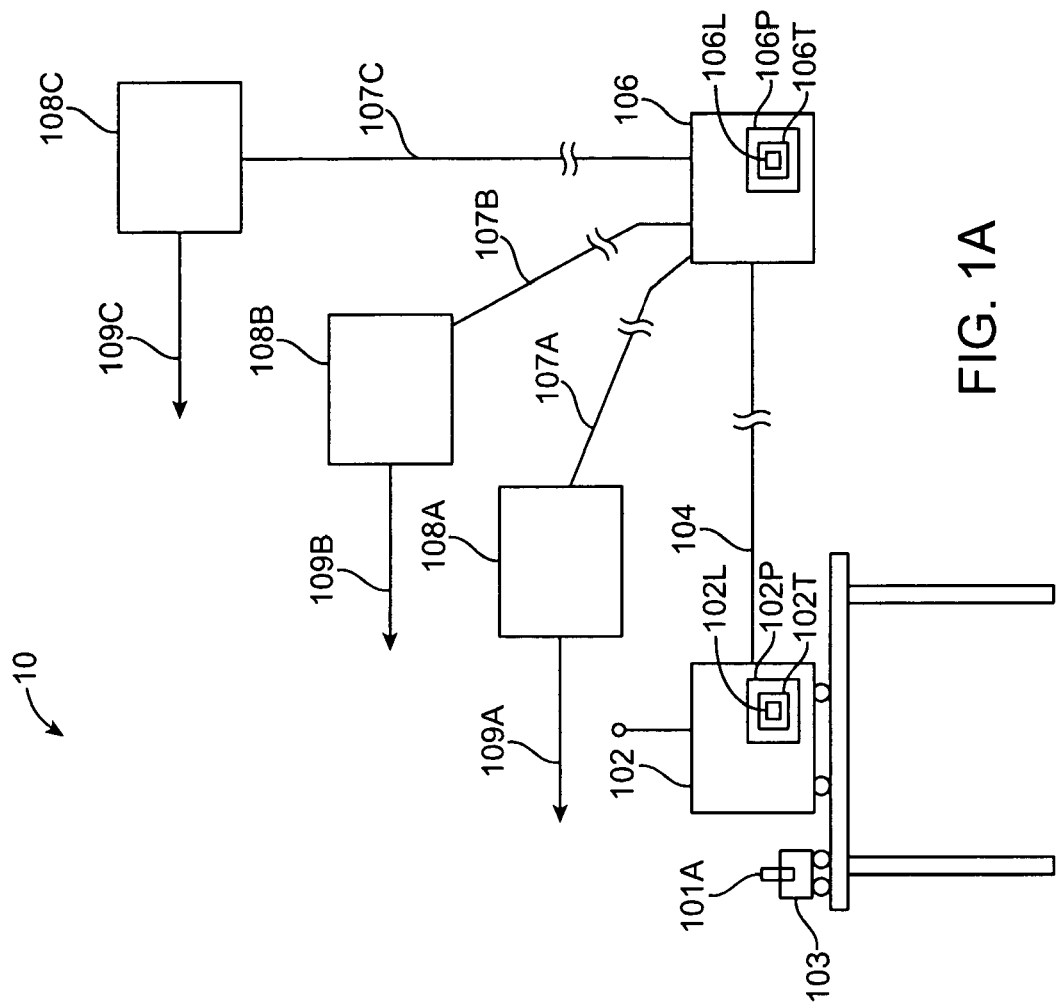
FIG. 1A shows a patient and a monitoring system comprising an adherent device, according to embodiments of the present invention.
Figure 1A:
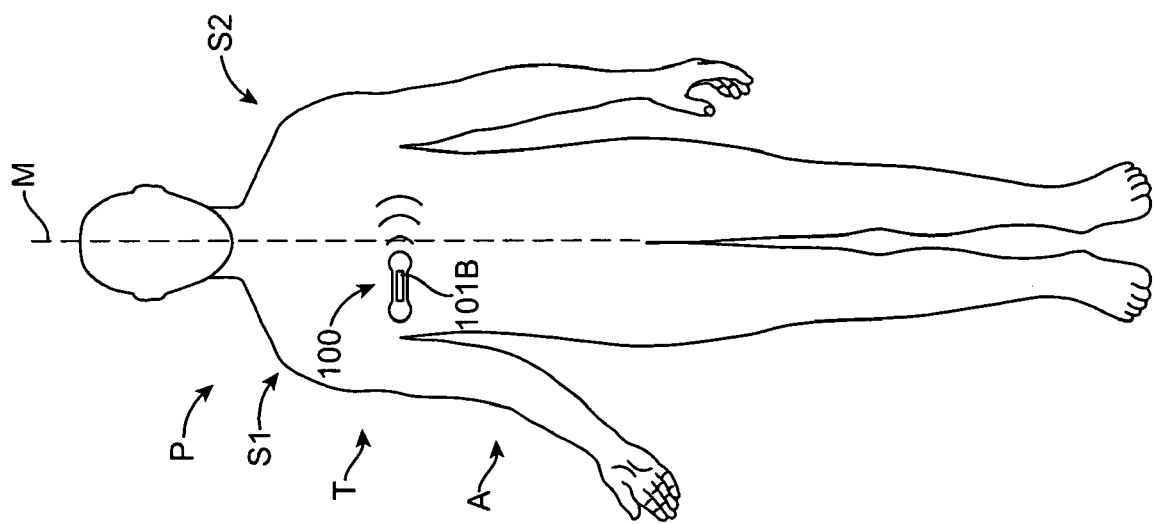

Embodiments of the present invention relate to patient monitoring. Although embodiments make specific reference to monitoring impedance, accelerometer and electrocardiogram signals with an adherent device, the system methods and device described herein may be applicable to any application in which physiological monitoring is used, for example wireless physiological monitoring for extended periods.

Embodiments of the present invention can be used with systems where many patients are measured and many gateways are used, such that the transmission of data from the devices occurs in a controlled manner that maintains the integrity of communication channels from each measurement device to a server system.

A patient device is configured to measure patient data. To measure patient data, the patient device can be at least one of worn by the patient, attached to the patient, implanted in the patient or worn by the patient. Therefore, many devices that transmit wireless data through a gateway can be incorporated with embodiments. For example, a gateway device can receive data from at least one patient worn device, for example a plurality of patient worn devices. Examples of patient worn devices that can be used to transmit wireless data include known wearable devices such as a Holter monitor or ambulatory electrocardiography device. The patient device may also comprise one or more implantable devices with wireless communication capabilities, for example as described in U.S. Pat. Nos. 6,164,284; 6,185,452; and 6,208,894. In an exemplary embodiment, the patient device may comprise injectable devices injected into the patient, which injectable devices are configured for wireless communication with an adherent device adhered to the patient, which adherent device communicates wirelessly with the gateway, for example as described in U.S. Pat. App. No. 60/972,316, filed on Sep. 14, 2007, entitled "Adherent Multi-Sensor Device with Implantable Device Communications Capabilities". The patient device may comprise one or more adherent devices simultaneously adhered to the patient, for example with a first adherent device adhered to a chest of the patient to measure patient physiology and a second adherent device adhered to a limb of the patient to measure patient movement, for example as described in U.S. Pat. App. No. 61/055,656, filed on May 23, 2008, entitled "Adherent Device for Sleep Disordered Breathing". The patient device may also comprise one or more of a plurality of patient worn device that are sequentially placed on the patient to measure physiologic status of the patient, for example as described in U.S. Pat. App. No. 60/972,537, filed on Sep. 14, 2007, entitled "Adherent Device with Multiple Physiological Sensors".

The gateway is configured to transmit data from the patient device to the backend server system at the remote site. The gateway comprises a list of approved devices. The data transmitted from the device can be controlled with a list, for example a list of approved devices.

In specific embodiments, an adherent device is configured to adhere to the skin of the patient with an adherent patch, for example breathable tape, to measure patient data. The device may comprise impedance circuitry coupled to at least four electrodes and can be configured to measure at least one of patient hydration or respiration, for example to detect sleep apnea and/or hypopnea. The impedance circuitry may be used to measure hydration of the patient, which can be useful evaluating the physiologic status of the patient, for example in combination with the detected sleep apnea and/or hypopnea. An accelerometer can be mechanically coupled to the adherent patch such that the accelerometer can be coupled to and move with the skin of the patient, thereby providing an accurate and reliable measurement of the orientation and/or activity of the patient, which can be helpful in determining that the patient is asleep. The accelerometer can be mechanically coupled to the adherent patch such that the accelerometer can detect motion of the jaw and/or legs. Electrocardiogram circuitry to generate an electrocardiogram signal may be coupled to at least two of the at least four electrodes, such that the sleep apnea and/or hypopnea can be detected in response to a heart rate variability from the electrocardiogram signal.

Embodiments of the present invention can be used to transmit important data relevant to patients with health conditions. For example, decompensation is failure of the heart to maintain adequate blood circulation. Although the heart can maintain at least some pumping of blood, the quantity is inadequate to maintain healthy tissues. Several symptoms can result from decompensation including pulmonary congestion, breathlessness, faintness, cardiac palpitation, edema of the extremities, and enlargement of the liver. Cardiac decompensation can result in slow or sudden death. Sudden Cardiac Arrest (hereinafter "SCA"), also referred to as sudden cardiac death, is an abrupt loss of cardiac pumping function that can be caused by a ventricular arrhythmia, for example ventricular tachycardia and/or ventricular fibrillation. Although decompensation and SCA can be related in that patients with decompensation are also at an increased risk for SCA, decompensation is primarily a mechanical dysfunction caused by inadequate blood flow, and SCA is primarily an electrical dysfunction caused by inadequate and/or inappropriate electrical signals of the heart.

In many embodiments, the adherent devices described herein may be used for 90 day monitoring, or more, and may comprise completely disposable components and/or reusable components, and can provide reliable data acquisition and transfer. In many embodiments, the patch is configured for patient comfort, such that the adherent patch can be worn and/or tolerated by the patient for extended periods, for example 90 days or more. The patch may be worn continuously for at least seven days, for example 14 days, and then replaced with another patch. Adherent devices with comfortable patches that can be worn for extended periods and in which patches can be replaced and the electronics modules reused are described in U.S. Pat. App. Nos. 60/972,537, entitled "Adherent Device with Multiple Physiological Sensors"; and 60/972,629, entitled "Adherent Device with Multiple Physiological Sensors", both filed on Sep. 14, 2007, the full disclosures of which have been previously incorporated herein by reference. In many embodiments, the adherent patch comprises a tape, which comprises a material, preferably breathable, with an adhesive, such that trauma to the patient skin can be minimized while the patch is worn for the extended period. The printed circuit board may comprise a flex printed circuit board that can flex with the patient to provide improved patient comfort.

FIG. 1A shows a patient P and a monitoring system 10. Patient P comprises a midline M, a first side S1, for example a right side, and a second side S2, for example a left side. Monitoring system 10 comprises an adherent patient device 100. Adherent patient device 100 can be adhered to a patient P at many locations, for example thorax T of patient P. In many embodiments, the adherent device may adhere to one side of the patient, from which side data can be collected. Work in relation with embodiments of the present invention suggests that location on a side of the patient can provide comfort for the patient while the device is adhered to the patient.

Monitoring system 10 includes components to transmit data to a remote center 106. Remote center 106 can be located in a different building from the patient, for example in the same town as the patient, and can be located as far from the patient as a separate continent from the patient, for example the patient located on a first continent and the remote center located on a second continent. Adherent patient device 100 can communicate wirelessly to an intermediate device 102, for example with a single wireless hop from the adherent device on the patient to the intermediate device. Intermediate device 102 comprises a communication gateway. Intermediate device 102 comprising the communication gateway can communicate with remote center 106 with a connection 104 in many ways. For example, connection 104 may comprise at least one of an internet connection or with a cellular connection.

In many embodiments, monitoring system 10 comprises a distributed processing system with at least one processor comprising a tangible medium of device 100, at least one processor 102P of intermediate device 102, and at least one processor 106P at remote center 106, each of which processors can be in electronic communication with the other processors. At least one processor 102P comprises a tangible medium 102T, and tangible medium 102T may be configured so as to comprise a list 106L of approved devices and/or device identifiers. The list 106L is used to control and/or limit which adherent devices communicate with intermediate device 102. At least one processor 106P comprises a tangible medium 106T, and tangible medium 106T may be configured so as to comprise a master list 106L of approved device identifiers. The master list and/or components of master list 106L can be transmitted to tangible medium 102T from processor 106P so as to control which devices are allowed to communicate with intermediate device 102, which may comprise an intermediate gateway device.

Remote processor 106P may comprise a backend server located at the remote center. Remote center 106 can be in communication with a health care provider 108A with a communication system 107A, such as the Internet, an intranet, phone lines, wireless and/or satellite phone. Health care provider 108A, for example a family member, nurse or caregiver, can be in communication with patient P with a communication system, for example with a two way communication system, as indicated by arrow 109A, for example by cell phone, email, landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the patient's thorax and contains sensing electrodes, battery, memory, logic, and wireless communication capabilities. In some embodiments, the patch can communicate with the remote center, via the intermediate device in the patient's home. In some embodiments, remote center 106 receives the patient data and applies a patient evaluation algorithm, for example an algorithm to calculate the apnea hypopnea index. When a flag is raised, the center may communicate with the patient, hospital, nurse, and/or physician to allow for therapeutic intervention.

The adherent device may be affixed and/or adhered to the body in many ways. For example, with at least one of the following: an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide|remove old patch|place new patch|remove guide), or a keyed attachment for chatter reduction. The patch and/or device may comprise an adhesiveless embodiment (e.g. chest strap), and/or a low-irritation adhesive for sensitive skin. The adherent patch and/or device can comprise many shapes, for example at least one of a dogbone, an hourglass, an oblong, a circular or an oval shape.

In many embodiments, the adherent device may comprise a reusable electronics module with replaceable patches, and each of the replaceable patches may include a battery. The module may collect cumulative data for approximately 90 days and/or the entire adherent component (electronics+ patch) may be disposable. In a completely disposable embodiment, a "baton" mechanism may be used for data transfer and retention, for example baton transfer may include baseline information. In some embodiments, the device may have a rechargeable module, and may use dual battery and/or electronics modules, wherein one module 101A can be recharged using a charging station 103 while the other module 101B is placed on the adherent patch with connectors. In some embodiments, the intermediate device 102 may comprise the charging module, data transfer, storage and/or transmission, such that one of the electronics modules can be placed in the intermediate device for charging and/or data transfer while the other electronics module is worn by the patient.

System 10 can perform the following functions: initiation, programming, measuring, storing, analyzing, communicating, predicting, and displaying. The adherent device may contain a subset of the following physiological sensors: bioimpedance, respiration, respiration rate variability, heart rate (ave, min, max), heart rhythm, heart rate variability (HRV), heart rate turbulence (HRT), heart sounds (e.g. S3), respiratory sounds, blood pressure, activity, posture, wake/sleep, orthopnea, temperature/heat flux, and weight. The activity sensor may comprise one or more of the following: ball switch, accelerometer, minute ventilation, HR, bioimpedance noise, skin temperature/heat flux, BP, muscle noise, posture.

The adherent device can wirelessly communicate with remote center 106. The communication may occur directly (via a cellular or Wi-Fi network), or indirectly through intermediate device 102. Intermediate device 102 may consist of multiple devices, which can communicate wired or wirelessly to relay data to remote center 106.

In many embodiments, instructions are transmitted from remote site 106 to a processor supported with the adherent patch on the patient, and the processor supported with the patient can receive updated instructions for the patient treatment and/or monitoring, for example while worn by the patient.

FIG. 1A1 shows monitoring a plurality of patients with monitoring system 10. The plurality of patients comprises at least two patients, for example a first patient PA, a second patient PB, a third patient PC and a fourth patient PD. Each of the plurality of patients has at least one device adhered or implanted into the patient to measure patient data. Intermediate device 102 comprises a plurality of at least two intermediate devices, for example a first intermediate device comprising a first gateway 102A, a second intermediate device comprising a second gateway 102B, a third intermediate device comprising a third gateway 102C; and a fourth intermediate device comprising a fourth gateway 104D. Each of the plurality of intermediate devices may comprise an approved patient device list that controls communication of the device with the gateway. For example first gateway 102A comprises a first approved device list 102AL. Second gateway 102B comprises a second approved device list 102BL. Third gateway 102C comprises a third approved device list 102CL. Fourth gateway 102D comprises a fourth approved device list 102DL. Each gateway allows the patient device to communicate with the back end server system at the remote center 106 when the device is on the approved device list, and each gateway may exclude communication with the backend server system at the remote center 106 when the patient device is not identified on the approved device list for the gateway. Remote center 106 comprises a master approved device 106L list that comprises each patient device approved for each gateway.

Each gateway may comprise a processor comprising a tangible medium configured to determine when the device is on the approved patch list. For example, first gateway 102A comprises a first processor 102AP. Second gateway 102B comprises a second processor 102BP. Third gateway 102C comprises a third processor 102CP. Fourth gateway 102D comprises a fourth processor 102DP.

Each of gateways 102A, 102B, 102C and 102D can send data to remote center 106 through each of connections 104A, 104B, 104C and 104D, respectively. Connections 104A, 104B, 104C and 104D may be, for example, a wireless connection, a cellular connection, a ZigBee connection, a BlueTooth connection, an Internet connection, an intranet connection, a wired connection, a cable connection or the like. The connection between the gateway and the backend server may comprise a dedicated connection when the gateway is paired to the adherent patient device, for example a dedicated cellular connection from a phone number dialed by the gateway.

More than one patient device can correspond to each patient. For example, each patient of the plurality can be sent home with a box of adherent patches, and each patch may comprise a unique identifier which is associated with the patient so as to correspond to the patient. The adherent patches can be adhered to the patient sequentially. For example, a first patch may be replaced after about one week with a second patch from the box. In some embodiments, a patient may have more than one patch simultaneously adhered to the patient, for example to measure data at two or more separate locations on the patient.

System 10 comprises a first plurality of patches for first patient PA, a second plurality of patches for second patient PB, a third plurality of patches for patient PC and a fourth plurality of patches provided for patient PD. The first plurality of adherent devices comprises adherent devices 100A1, 100A2, 100A3 and 100A4. Each of adherent devices 100A1, 100A2, 100A3 and 100A4 are configured to adhere to a patient, for example patient PA. The second plurality of adherent devices comprises adherent devices 100B1, 100B2, 100B3 and 100B4. Each of adherent devices 100B1, 100B2, 100B3 and 100B4 are configured to adhere to a patient, for example patient PB. The third plurality of adherent devices comprises adherent devices 100C1, 100C2, 100C3 and 100C4. Each of adherent devices 100C1, 100C2, 100C3 and 100C4 are configured to adhere to a patient, for example patient PC. The fourth plurality of adherent devices comprises adherent devices 100D1, 100D2, 100D3 and 100D4. Each of adherent devices 100D1, 100D2, 100D3 and 100D4 are configured to adhere to adhere to a patient, for example patient PD.

As noted above, each adherent device may have a device identifier, for example a unique device identifier such as a serial number. The device identifier can be transmitted with the patient data so as to allow the remote server system to identify the device. The device identifier may be encrypted. The adherent devices can be manufactured with a device identifier built into them, for example a device identifier stored in EPROM or non-volatile storage.

Each of gateways 102A, 102B, 102C, and 102D may each include an approved patient device list, such as a list of approved patient device serial numbers, and/or range of approved patient device identifiers. Each adherent patient device may transmit the device identifier to any gateway within range of the wireless communication signal transmitted by the adherent device.

When a specific adherent device is in the list and/or within the range of device identifiers of a specific gateway, the gateway can "pair" to the specific adherent device, such that data is transmitted from the adherent device to the backend server system at remote center 106. For example, patient data from one of the adherent devices can be transmitted to remote center 106, which may comprise the backend server or system. When the patient device is paired to the gateway, the gateway can provide a dedicated connection to from the gateway to the backend server system, such that the communication channel integrity is maintained.

Each device can pair with at least one of the gateways, in response to the approved list of the gateway. Each of adherent devices 100A1, 100A2, 100A3 and 100A4 may pair with the intermediate device comprising gateway 102A with pairing 100A1P, 100A2P, 100A3P and 100A4P, respectively, in response to approved patient device list 102AL. As noted above, the pairing can be sequential, for example when one of the adherent devices replaces a prior adherent device after an extended period of about one week. Each of adherent devices 100B1, 100B2, 100B3 and 100B4 may pair with the intermediate device comprising gateway 102B with pairing 100B1P, 100B2P, 100B3P and 100B4P, respectively, in response to approved patient device list 102BL. Each of adherent devices 100C1, 100C2, 100C3 and 100C4 may pair with the intermediate device comprising gateway 102C with pairing 100C1P, 100C2P, 100C3P and 100C4P, respectively, in response to approved patient device list 102CL. Each of adherent devices 100D1, 100D2, 100D3 and 100D4 may pair with the intermediate device comprising gateway 102D with pairing 100D1P, 100D2P, 100D3P and 100D4P, respectively, in response to approved device list 102DL.

Each of the adherent devices can communicate with the backend server when paired to the intermediate device comprising the gateway. Each of adherent devices 100A1, 100A2, 100A3 and 100A4 may be in paired electronic communication with the intermediate device comprising gateway 102A and transmit data to the backend server at remote center 106 when paired. Each of adherent devices 100B1, 100B2, 100B3 and 100B4 may be in sequential paired electronic communication with the intermediate device comprising gateway 102B and transmit data to the backend server at remote center 106 when paired. Each of adherent devices 100C1, 100C2, 100C3 and 100C4 may be in sequential paired electronic communication with the intermediate device comprising gateway 102C and transmit data to the backend server at remote center 106 when paired. Each of adherent devices 100D1, 100D2, 100D3 and 100D4 may be in electronic communication with the intermediate device comprising gateway 102D and transmit data to the backend server at remote center 106 when paired.

Although the pairing of the patient device to the gateways can occur in many ways, the protocol for pairing of each of the adherent devices with each of the gateways can be similar. For example, when patch 100A1 communicates with gateway 100A, adherent patient device 100A1 can be configured transmits its serial number SN to gateway 100A. The processor of gateway 102A may query approved device list 102AL and performs logic operations. If the serial number of device 100A is in the approved patient list 102AL, then device 100A will be allowed to pair with gateway 102A to send data to remote center 106. When the serial number of device 100A is not in the approved patient list 102AL, device 100A is excluded from pairing with gateway 102. In many embodiments, when device 100A pairs with gateway 102 to send data to remote center 106, gateway 102 adds the device identifier of device 100A to a packet of data from gateway 102 so that remote center 106 detect pairing between device 100A and gateway 102. Similar protocols can be used to transmit data for additional patient devices and gateways.

As the pairing of each device with the gateway is controlled with the approved patient device list, one intermediate device can be allowed to communicate with a plurality of patient devices for a plurality of patients. For example, the second intermediate device comprising second gateway 102B can be configured to communicate with device 100A1 when approved device list 102BL comprises the identifier for device 100A1 for first patient PA. The first intermediate device comprising first gateway 102A can be configured to communicate with device 100B1 when approved device list 102AL comprises the identifier for device 100B 1 for second patient PB. With such a configuration, patient devices 100C1-100C4 for patient PC and patient devices 100D1-100D4 for patient PD can be excluded from paired communication the first intermediate device comprising gateway 102A and the second intermediate device comprising gateway 102B. Such configurations can be helpful when patients are mobile, for example in a ward of a hospital where many patient devices can be within range of a gateway device.

The gateways configured to pair with devices in response to the approved patch list allows for great flexibility in controlling the communication. For example, the adherent device can be paired to either zero or one gateway, in response to the approved patch list at each gateway, while a single gateway may be paired with many adherent patches. For example, a gateway using a Bluetooth connection may have at least 8 simultaneous connections for 8 adherent devices from 8 patients. The adherent patient device may actively search for a gateway to pair with, for example by searching and sorting gateway signals from strongest to weakest and stopping the search process when the adherent patient device has paired with the gateway with the strongest signal and in which the approved device list allows communication.

The gateways configured to pair with devices in response to the approved patch list allows for the communication to be controlled dynamically with dynamic updating of the approved device list. For example gateway 102A may comprise an approved device list 102AL which may be sent from remote center 106 or another server through two-way connection 104A. Approved device list 102AL may comprise, for example, a binary file, a hexadecimal file, an ASCII file or an encrypted file stored on tangible medium. Approved device list 102AL may comprise a list of serial numbers of approved adherent devices. Approved device list 102AL can be dynamic. For example, the list of serial numbers of approved adherent devices of list 102AL may change and/or be updated at any time, for example, with instructions from the backend server located at remote center 106. List 102AL may be sent from remote center 106 at any time to instruct a gateway 102A as to which adherent devices to pair with. For example, the list can be updated when a new patch is applied to a patient and/or when a patient is supplied with a box of adherent devices. In some instances, the gateway can be located in the patient's home and the list updated when the patient is sent home with a box of patches and gateway.

Each of gateways 102A, 102B, 102C, and 102D may have its own device identifier, for example a unique device identifier such as a serial number. The device identifier may be encrypted. Gateways 102A, 102B, 102C, and 102D can be manufactured with a device identifier built into them, for example a device identifier stored in EPROM or non-volatile storage. An adherent device and a gateway may be configured to exchange a link key so as to pair the gateway with the patient device.

Although FIG. 1A1 shows four patients PA, PB, PC and PD, each with a set of four adherent devices configured to attached to him or her, many patients, for example at least 100 patients, and many gateways, for example at least 25 gateways, may be provided.

Figure 2:
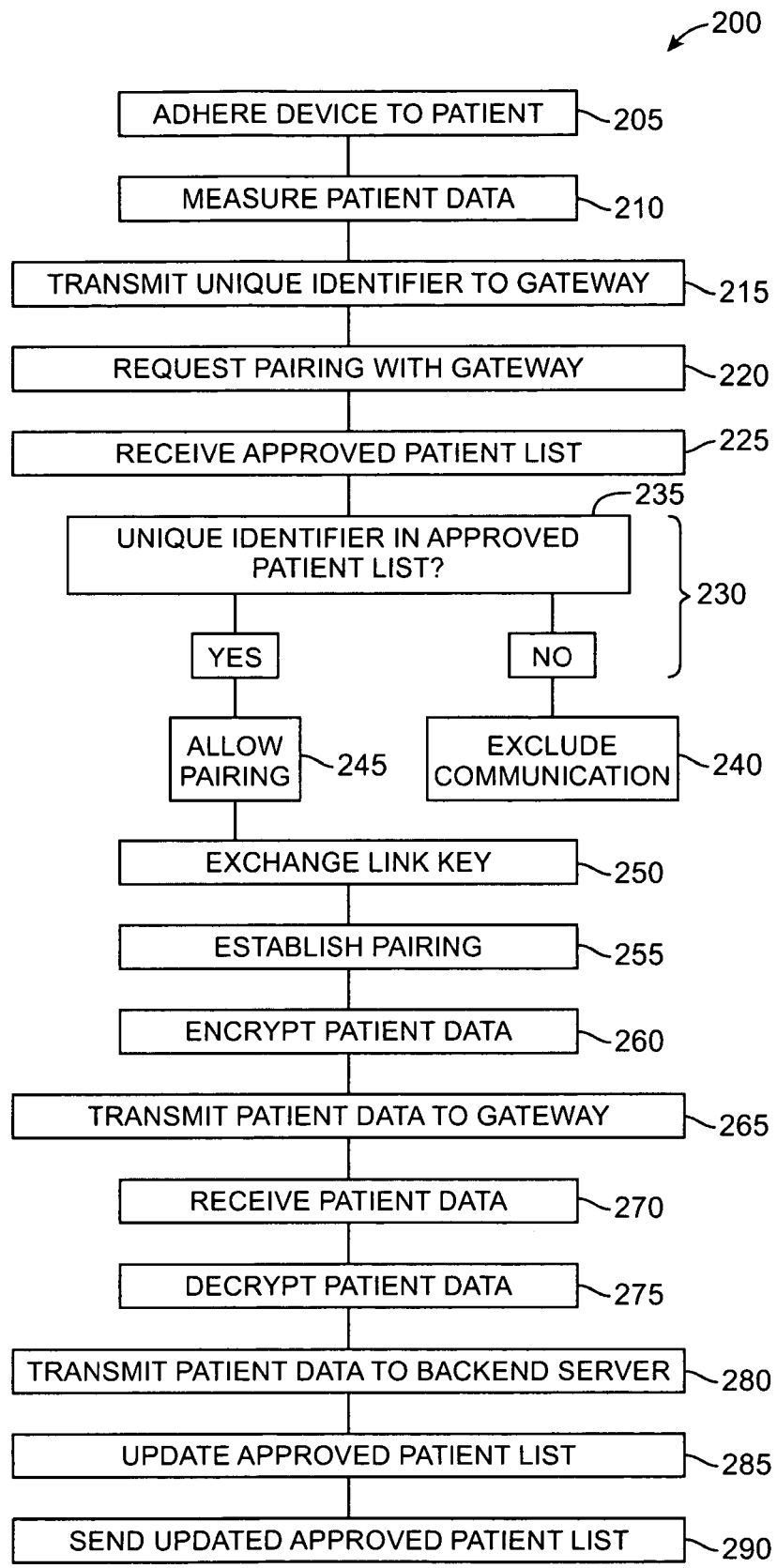

FIG. 1A2 shows master approved patient device list 106L and first approved patient device list 102AL transmitted to first gateway 102A, second approved patient device list 102BL transmitted to second gateway 102B, third approved patient device list 102CL transmitted to third gateway 102C, and fourth approved patient device list 102DL transmitted to fourth gateway 102D. The master approved patient device list 106L may comprise a field for each of a unique patient identifier, unique patient device identifier and a unique gateway identifier. The master list may comprise an entry with the unique patient device identifier, the unique gateway identifier and the unique patient device identifier for each patient device, for example patient PTA with patient device 100A1 and gateway 102A.

Connections from the backend server at the remote site can update the list at each gateway to dynamically control communication with the patient devices at each gateway. The backend server at remote center 106 can use connection 104A from remote center 106 to gateway 102A to dynamically update list 102AL at gateway 102A. Connection 104B from remote center 106 to gateway 102B can similarly be used to dynamically update list 102BL at gateway 102B. Connection 104C from remote center 106 to gateway 102C can also be used to dynamically update list 102CL at gateway 102C. The backend server at remote center 106 can use connection can also use connection 104D from remote center 106 to gateway 102D to dynamically update list 102DL at gateway 102D.

As shown in FIG. 1A2, one entry may include: a unique patient identifier PTA associated with a unique device identifier 100A1 and a unique gateway identifier 102A. Other entries include: a unique patient identifier PTA associated with a unique device identifier 100A2 and a unique gateway identifier 102A; a unique patient identifier PTA associated with a unique device identifier 100A3 and a unique gateway identifier 102A; a unique patient identifier PTA associated with a unique device identifier 100A4 and a unique gateway identifier 102A; a unique patient identifier PTB associated with a unique device identifier 100B1 and a unique gateway identifier 102B; a unique patient identifier PTB associated with a unique device identifier 100B2 and a unique gateway identifier 102B; a unique patient identifier PTB associated with a unique device identifier 100B3 and a unique gateway identifier 102B; a unique patient identifier PTB associated with a unique device identifier 100B4 and a unique gateway identifier 102B; a unique patient identifier PTC associated with a unique device identifier 100C1 and a unique gateway identifier 102C; a unique patient identifier PTC associated with a unique device identifier 100C2 and a unique gateway identifier 102C; a unique patient identifier PTC associated with a unique device identifier 100C3 and a unique gateway identifier 102C; a unique patient identifier PTC associated with a unique device identifier 100C4 and a unique gateway identifier 102C; a unique patient identifier PTD associated with a unique device identifier 100D1 and a unique gateway identifier 102D; a unique patient identifier PTD associated with a unique device identifier 100D2 and a unique gateway identifier 102D; a unique patient identifier PTD associated with a unique device identifier 100D3 and a unique gateway identifier 102D; and a unique patient identifier PTD associated with a unique device identifier 100D4 and a unique gateway identifier 102D.

The approved patient device lists and the master list can be configured in many ways. For example, the approved patient device list at each gateway may comprise master approved device list 106L such that the list at each gateway is the same and the processor at each gateway compares the gateway identifier to the patients on the master list that correspond to the gateway identifier.

As shown in FIG. 1A2, the approved patient device list at each gateway may include the unique patient device identifiers and a unique patient identifier. Gateway 102A comprises list 102AL. List 102AL comprises unique device identifiers 100A1, 100A2, 100A3, and 100A4 for each device given to the patient corresponding to unique patient identifier PTA. Gateway 102B comprises list 102BL. List 102BL comprises unique patient device identifiers 100B1, 100B2, 100B3, and 100B4 for each device given to the patient corresponding to the unique patient identifier PTB. Gateway 102C comprises list 102CL. List 102CL comprises the unique patient device identifiers 100C1, 100C2, 100C3, and 100C4 for each device given to the patient corresponding to the unique patient identifier PTA. Gateway 102D comprises list 102DL. List 102DL comprises unique patient device identifiers 100D1, 100D2, 100D3, and 100D4 for each device given to the patient corresponding to the unique patient identifier PTD.

FIG. 1A3 shows master list 106L updated to a second configuration from a first configuration shown in FIG. 1A2, so as to accommodate additional devices and/or to remove devices from the list and to disable communication of the devices removed from the list. The list at each gateway can be updated in response to the updated master list. There may be more than one unique patient device identifier for a given unique patient identifier, and there may be only one unique patient device identifier for a given unique patient identifier.

Master list 106L can be updated to allow a plurality of patient devices to communicate with each gateway, for example four patient devices. For example, entries of the updated master approved patient device list 106L may include: a unique patient identifier PTA, a unique device identifier 100A1, and a unique gateway identifier 102A; a unique patient identifier PTE, a unique device identifier 100E1, and a unique gateway identifier 102A; a unique patient identifier PTI, a unique device identifier 100I1, and a unique gateway identifier 102A; a unique patient identifier PTM, a unique device identifier 100M1, and a unique gateway identifier 102A; a unique patient identifier PTB, a unique device identifier 100B1, and a unique gateway identifier 102B; a unique patient identifier PTF, a unique device identifier 100F1, and a unique gateway identifier 102B; a unique patient identifier PTJ, a unique device identifier 100J1, and a unique gateway identifier 102B; a unique patient identifier PTN, a unique device identifier 100N1, and a unique gateway identifier 102B; a unique patient identifier PTC, a unique device identifier 100C1, and a unique gateway identifier 102C; a unique patient identifier PTG, a unique device identifier 100G1, and a unique gateway identifier 102C; a unique patient identifier PTK, a unique device identifier 100K1, and a unique gateway identifier 102C; a unique patient identifier PTO, a unique device identifier 10001, and a unique gateway identifier 102C; a unique patient identifier PTD, a unique device identifier 100D1, and a unique gateway identifier 102D; a unique patient identifier PTH, a unique device identifier 100H1, and a unique gateway identifier 102D; a unique patient identifier PTL, a unique device identifier 100L1, and a unique gateway identifier 102D; and a unique patient identifier PTP, a unique device identifier 100P1, and a unique gateway identifier 102D.

The list at each gateway can be updated in response to the master list to allow a plurality of patient devices to communicate with each gateway, for example two three, and four our more devices per gateway. For example, each gateway may include a plurality of entries for unique patient device identifiers and unique device identifiers in response to the updated master list 106L. For example, gateway 102A comprises updated list 102AL comprising unique device identifier 100A1, 100E1, 10011, and 100M1 for unique patient identifier PTA, PTE, PTI, and PTM, respectively. Gateway 102B comprises updated list 102BL comprising unique device identifier 100B1, 100F1, 100J1, and 100N1 for unique patient identifier PTB, PTF, PTJ, and PTN, respectively. Gateway 102C comprises updated list 102CL comprising unique device identifier 100C1, 100G1, 100K1, and 10001 for unique patient identifier PTC, PTG, PTK, and PTO. Gateway 102D comprises updated list 102DL comprising unique device identifier 100D1, 100H1, 100L1, and 100P1 for unique patient identifier PTD, PTH, PTL, and PTP, respectively.

Figure 1B:
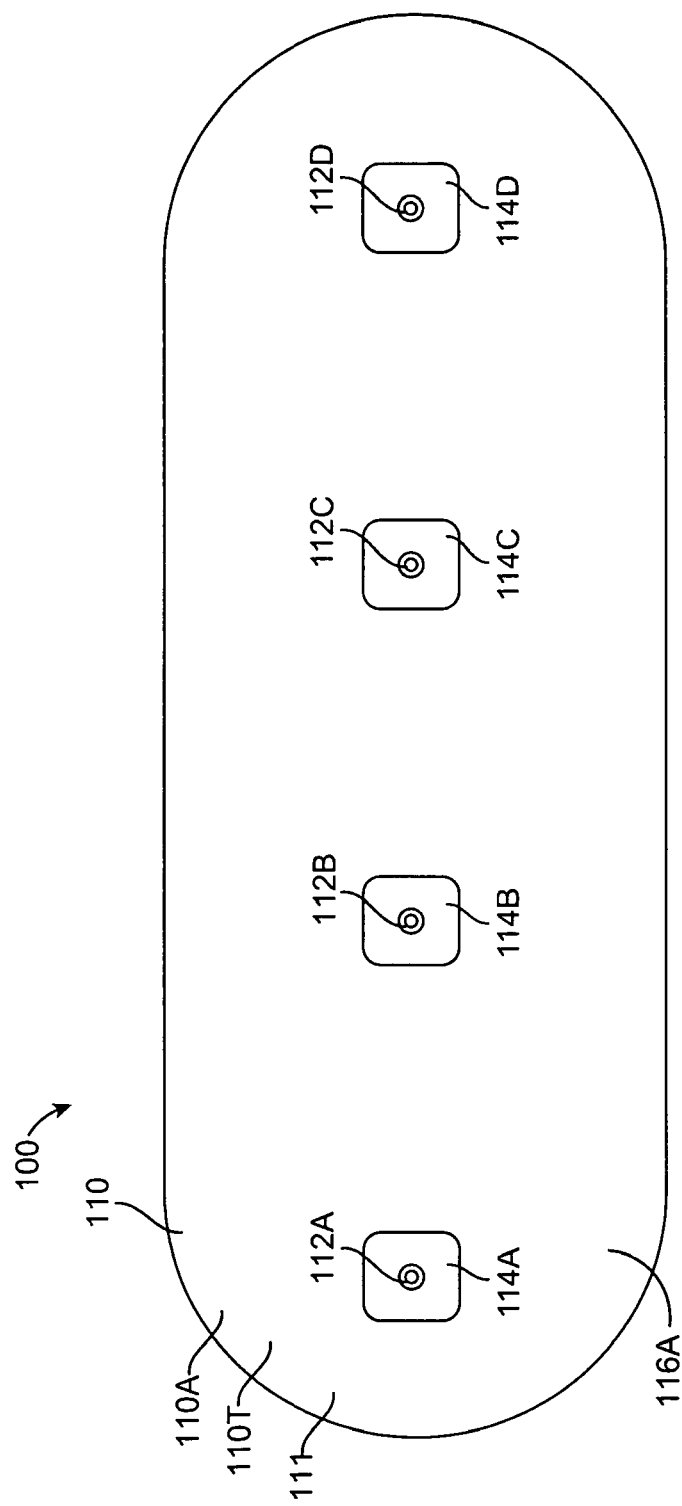
FIG. 1B shows a bottom view of the adherent device as in FIG. 1A comprising an adherent patch.

FIG. 1B shows a bottom view of adherent patient device 100 as in FIG. 1A comprising an adherent patch 110. Each of the adherent patient devices described above may be similar to adherent patch 100. Adherent patch 110 comprises a first side, or a lower side 110A, that is oriented toward the skin of the patient when placed on the patient. In many embodiments, adherent patch 110 comprises a tape 110T which is a material, preferably breathable, with an adhesive 116A. Patient side 110A comprises adhesive 116A to adhere the patch 110 and adherent patient device 100 to patient P. Electrodes 112A, 112B, 112C and 112D are affixed to adherent patch 110. In many embodiments, at least four electrodes are attached to the patch, for example six electrodes. In some embodiments, the patch comprises two electrodes, for example two electrodes to measure the electrocardiogram (ECG) of the patient. Gel 114A, gel 114B, gel 114C and gel 114D can each be positioned over electrodes 112A, 112B, 112C and 112D, respectively, to provide electrical conductivity between the electrodes and the skin of the patient. In many embodiments, the electrodes can be affixed to the patch 110, for example with known methods and structures such as rivets, adhesive, stitches, etc. In many embodiments, patch 110 comprises a breathable material to permit air and/or vapor to flow to and from the surface of the skin.

Figure 1C:
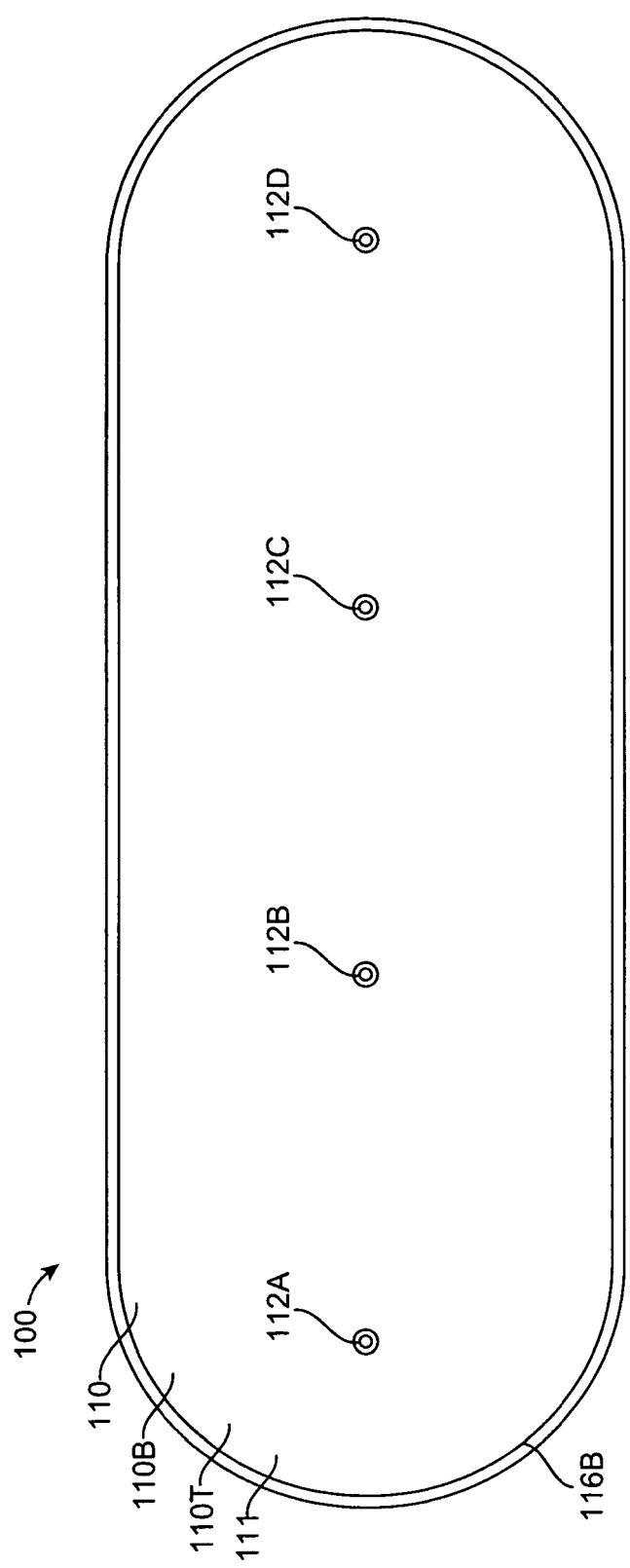
FIG. 1C shows a top view of the adherent patch, as in FIG. 1B.

FIG. 1C shows a top view of the adherent patch 100, as in FIG. 1B. Adherent patch 100 comprises a second side, or upper side 110B. In many embodiments, electrodes 112A, 112B, 112C and 112D extend from lower side 110A through adherent patch 110 to upper side 110B.

An adhesive 116B can be applied to upper side 110B to adhere structures, for example a breathable cover, to the patch such that the patch can support the electronics and other structures when the patch is adhered to the patient. The PCB may comprise completely flex PCB, rigid PCB, rigid PCB combined flex PCB and/or rigid PCB boards connected by cable.

FIG. 1D shows a printed circuit boards and electronic components over adherent patch 110, as in FIG. 1A to 1C. In some embodiments, a printed circuit board (PCB), for example flex printed circuit board 120, may be connected to electrodes 112A, 112B, 112C and 112D with connectors 122A, 122B, 122C and 122D. Flex printed circuit board 120 can include traces 123A, 123B, 123C and 123D that extend to connectors 122A, 122B, 122C and 122D, respectively, on the flex PCB. Connectors 122A, 122B, 122C and 122D can be positioned on flex printed circuit board 120 in alignment with electrodes 112A, 112B, 112C and 112D so as to electrically couple the flex PCB with the electrodes. In some embodiments, connectors 122A, 122B, 122C and 122D may comprise insulated wires and/or a film with conductive ink that provide strain relief between the PCB and the electrodes. For example, connectors 122A, 122B, 122C and 122D may comprise a flexible polyester film coated with conductive silver ink. In some embodiments, additional PCB's, for example rigid PCB's 120A, 120B, 120C and 120D, can be connected to flex printed circuit board 120. Electronic components 130 can be connected to flex printed circuit board 120 and/or mounted thereon. In some embodiments, electronic components 130 can be mounted on the additional PCB's.

Electronic components 130 comprise components to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 comprise an activity sensor and activity circuitry 134, impedance circuitry 136 and electrocardiogram circuitry, for example ECG circuitry 136. In some embodiments, electronics circuitry 130 may comprise a microphone and microphone circuitry 142 to detect an audio signal from within the patient, and the audio signal may comprise a heart sound and/or a respiratory sound, for example an S3 heart sound and a respiratory sound with rales and/or crackles.

Electronics circuitry 130 may comprise a temperature sensor, for example a thermistor in contact with the skin of the patient, and temperature sensor circuitry 144 to measure a temperature of the patient, for example a temperature of the skin of the patient. A temperature sensor may be used to determine the sleep and wake state of the patient. The temperature of the patient can decrease as the patient goes to sleep and increase when the patient wakes up.

Work in relation to embodiments of the present invention suggests that skin temperature may effect impedance and/or hydration measurements, and that skin temperature measurements may be used to correct impedance and/or hydration measurements. In some embodiments, increase in skin temperature or heat flux can be associated with increased vaso-dilation near the skin surface, such that measured impedance measurement decreased, even through the hydration of the patient in deeper tissues under the skin remains substantially unchanged. Thus, use of the temperature sensor can allow for correction of the hydration signals to more accurately assess the hydration, for example extra cellular hydration, of deeper tissues of the patient, for example deeper tissues in the thorax.

Electronics circuitry 130 may comprise a processor 146. Processor 146 comprises a tangible medium, for example read only memory (ROM), electrically erasable programmable read only memory (EEPROM) and/or random access memory (RAM). Processor 146 may comprise many known processors with real time clock and frequency generator circuitry, for example the PIC series of processors available from Microchip, of Chandler, Ariz. In some embodiments, processor 136 may comprise the frequency generator and real time clock. The processor can be configured to control a collection and transmission of data from the impedance circuitry electrocardiogram circuitry and the accelerometer. In many embodiments, device 100 comprise a distributed processor system, for example with multiple processors on device 100.

Electronics circuitry 130 may comprise electromyogram (hereinafter "EMG") circuitry 148 to measure muscle activity. EMG circuitry 148 can measure signals from muscles and may be connected to and/or comprise at least two of electrode 112A, electrode 112B, electrode 112C or electrode 112D. EMG circuitry 148 comprises an amplifier to amplify signals from contracting muscles so as to generate an EMG signal. EMG circuitry 148 can be connected to processor to send the EMG signal to the processor for storage and/or analysis.

In many embodiments, electronics components 130 comprise wireless communications circuitry 132 to communicate with remote center 106. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, wireless communication circuitry is configured to transmit the hydration signal, the electrocardiogram signal and the inclination signal to the remote center with a single wireless hop, for example from wireless communication circuitry 132 to intermediate device 102. The communication protocol comprises at least one of Bluetooth, Zigbee, WiFi, WiMax, IR, amplitude modulation or frequency modulation. In many embodiments, the communications protocol comprises a two way protocol such that the remote center is capable of issuing commands to control data collection.

Intermediate device 102 may comprise a data collection system to collect and store data from the wireless transmitter. The data collection system can be configured to communicate periodically with the remote center. The data collection system can transmit data in response to commands from remote center 106 and/or in response to commands from the adherent device.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer may comprises a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example ECG data and/or bioimpedance data, for example a respiration rate of the patient.

Impedance circuitry 136 can generate both hydration data and respiration data. In many embodiments, impedance circuitry 136 is electrically connected to electrodes 112A, 112B, 112C and 112D in a four pole configuration, such that electrodes 112A and 112D comprise outer electrodes that are driven with a current and comprise force electrodes that force the current through the tissue. The current delivered between electrodes 112A and 112D generates a measurable voltage between electrodes 112B and 112C, such that electrodes 112B and 112C comprise inner, sense, electrodes that sense and/or measure the voltage in response to the current from the force electrodes. In some embodiments, electrodes 112B and 112C may comprise force electrodes and electrodes 112A and 112B may comprise sense electrodes. The voltage measured by the sense electrodes can be used to measure the impedance of the patient and determine the respiration rate and/or hydration of the patient.

FIG. 1D1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to cardiac decompensation, and that extracellular resistance 158 and extracellular fluid can be effectively measured with frequencies in a range from about 0.5 kHz to about 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention measure hydration with frequencies from about 0.5 kHz to about 20 kHz to determine patient hydration.

In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from two or more of electrodes 112A, 112B, 112C and 112D in many ways. In some embodiments, ECG circuitry 138 is connected to inner electrodes 112B and 122C, which may comprise sense electrodes of the impedance circuitry as described above. In some embodiments, ECG circuitry 138 can be connected to electrodes 112A and 112D so as to increase spacing of the electrodes. The inner electrodes may be positioned near the outer electrodes to increase the voltage of the ECG signal measured by ECG circuitry 138. In many embodiments, the ECG circuitry may measure the ECG signal from electrodes 112A and 112D when current is not passed through electrodes 112A and 112D, for example with switches as described in U.S. App. No. 60/972,527, the full disclosure of which has been previously incorporated herein by reference.

Figure 1E:
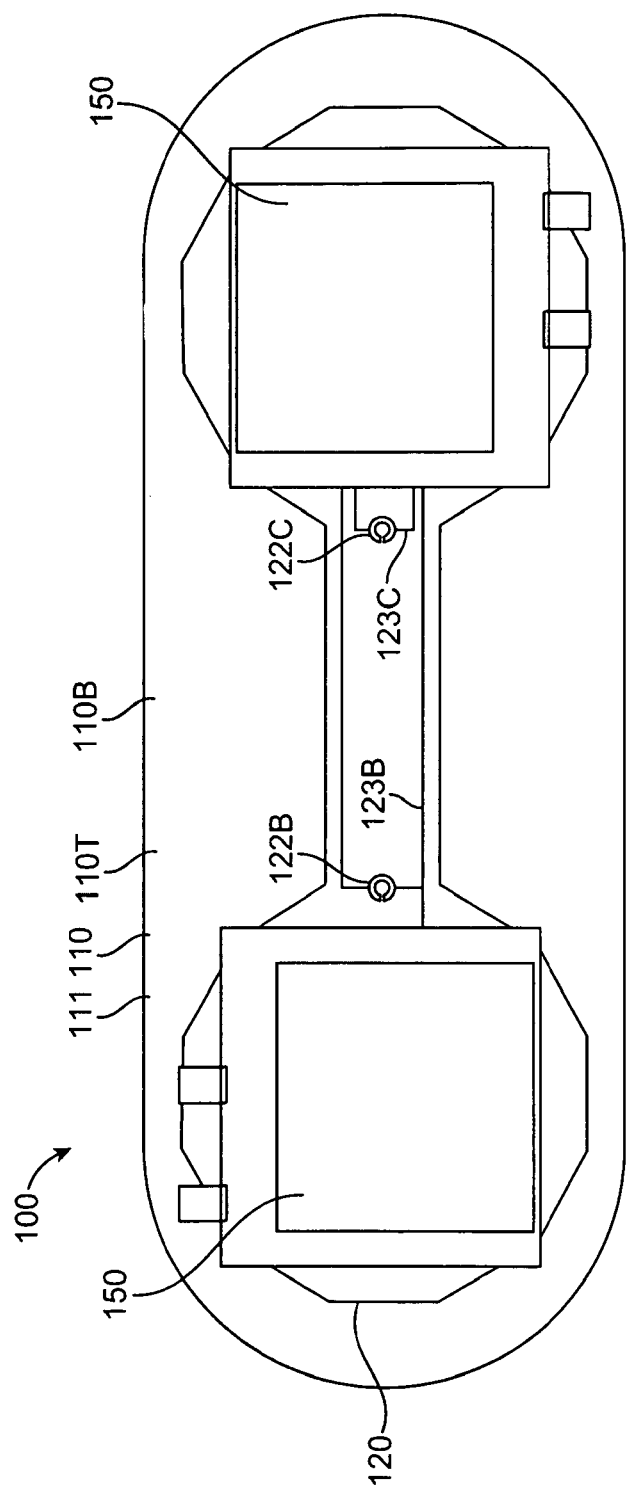
FIG. 1E shows batteries positioned over the printed circuit board and electronic components as in FIG. 1D.

FIG. 1E shows batteries 150 positioned over the flex printed circuit board and electronic components as in FIG. 1D. Batteries 150 may comprise rechargeable batteries that can be removed and/or recharged. In some embodiments, batteries 150 can be removed from the adherent patch and recharged and/or replaced.

FIG. 1F shows a top view of a cover 162 over the batteries, electronic components and flex printed circuit board as in FIGS. 1A to 1E. In many embodiments, an electronics housing 160 may be disposed under cover 162 to protect the electronic components, and in some embodiments electronics housing 160 may comprise an encapsulant over the electronic components and PCB. In some embodiments, cover 162 can be adhered to adherent patch 110 with an adhesive 164 on an underside of cover 162. In many embodiments, electronics housing 160 may comprise a water proof material, for example a sealant adhesive such as epoxy or silicone coated over the electronics components and/or PCB. In some embodiments, electronics housing 160 may comprise metal and/or plastic. Metal or plastic may be potted with a material such as epoxy or silicone.

Cover 162 may comprise many known biocompatible cover, casing and/or housing materials, such as elastomers, for example silicone. The elastomer may be fenestrated to improve breathability. In some embodiments, cover 162 may comprise many known breathable materials, for example polyester, polyamide, and/or elastane (Spandex). The breathable fabric may be coated to make it water resistant, waterproof, and/or to aid in wicking moisture away from the patch.

Figure 1H:
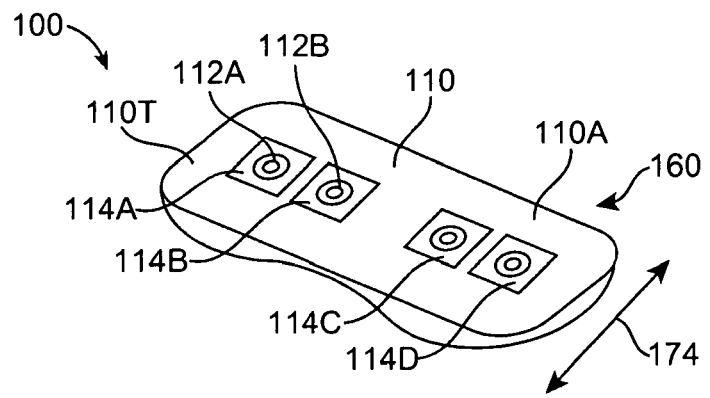
FIG. 1H shown a bottom isometric view of the adherent device as in FIGS. 1A to 1G.
Figure 1G:
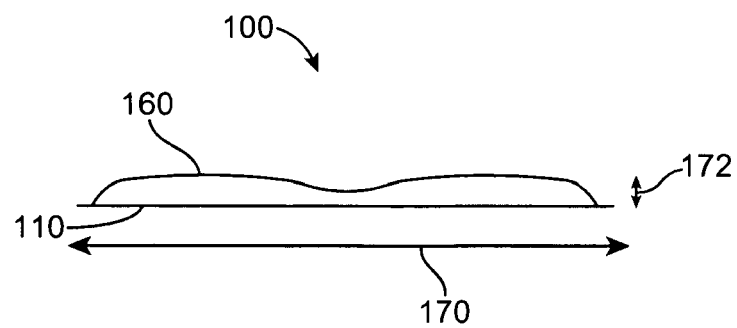
FIG. 1G shows a side view of the adherent device as in FIGS. 1A to 1F.

FIG. 1G shows a side view of adherent patient device 100 as in FIGS. 1A to 1F. Adherent patient device 100 comprises a maximum dimension, for example a length 170 from about 2 to 10 inches (from about 50 mm to about 250 mm), for example from about 4 to 6 inches (from about 100 mm to about 150 mm). In some embodiments, length 170 may be no more than about 6 inches (no more than about 150 mm). Adherent patient device 100 comprises a thickness 172. Thickness 172 may comprise a maximum thickness along a profile of the device. Thickness 172 can be from about 0.1 inches to about 0.4 inches (from about 5 mm to about 10 mm), for example about 0.3 inches (about 7.5 mm).

FIG. 1H shown a bottom isometric view of adherent patient device 100 as in FIGS. 1A to 1G. Adherent patient device 100 comprises a width 174, for example a maximum width along a width profile of adherent patient device 100. Width 174 can be from about 1 to about 4 inches (from about 25 mm to 100 mm), for example about 2 inches (about 50 mm).

Figure 1K:
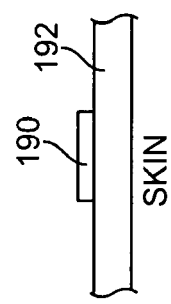
FIG. 1K shows at least one electrode configured to electrically couple to a skin of the patient through a breathable tape, according to embodiments of the present invention.
Figure 1I:
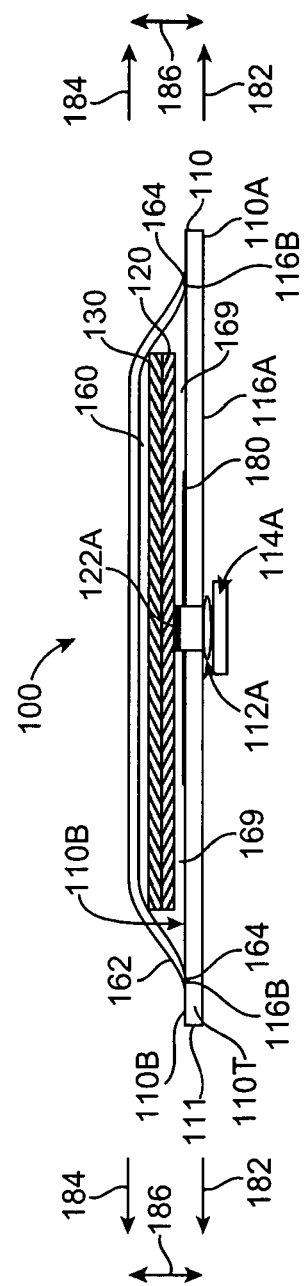
FIGS. 1I and 1J show a side cross-sectional view and an exploded view, respectively, of the adherent device as in FIGS. 1A to 1H.
Figure 1J:
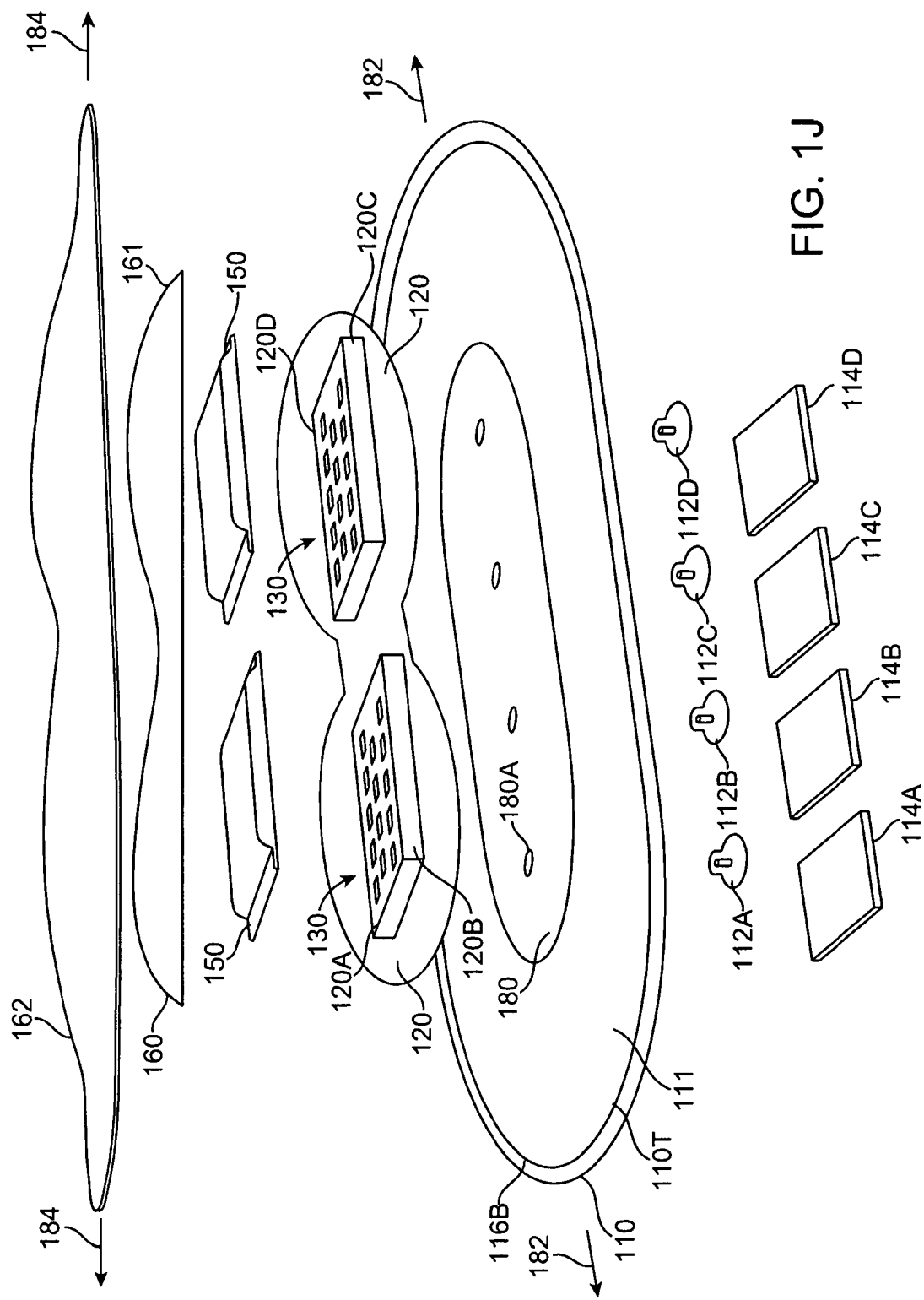

FIGS. 1I and 1J show a side cross-sectional view and an exploded view, respectively, of adherent patient device 100 as in FIGS. 1A to 1H. Device 100 comprises several layers. Gel 114A, or gel layer, is positioned on electrode 112A to provide electrical conductivity between the electrode and the skin. Electrode 112A may comprise an electrode layer. Adherent patch 110 may comprise a layer of breathable tape 110T, for example a known breathable tape, such as tricot-knit polyester fabric. An adhesive 116A, for example a layer of acrylate pressure sensitive adhesive, can be disposed on underside 110A of adherent patch 110.

A gel cover 180, or gel cover layer, for example a polyurethane non-woven tape, can be positioned over patch 110 comprising the breathable tape. A PCB layer, for example flex printed circuit board 120, or flex PCB layer, can be positioned over gel cover 180 with electronic components 130 connected and/or mounted to flex printed circuit board 120, for example mounted on flex PCB so as to comprise an electronics layer disposed on the flex PCB layer. In many embodiments, the adherent device may comprise a segmented inner component, for example the PCB may be segmented to provide at least some flexibility. In many embodiments, the electronics layer may be encapsulated in electronics housing 160 which may comprise a waterproof material, for example silicone or epoxy. In many embodiments, the electrodes are connected to the PCB with a flex connection, for example trace 123A of flex printed circuit board 120, so as to provide strain relive between the electrodes 112A, 112B, 112C and 112D and the PCB.

Gel cover 180 can inhibit flow of gel 114A and liquid. In many embodiments, gel cover 180 can inhibit gel 114A from seeping through breathable tape 110T to maintain gel integrity over time. Gel cover 180 can also keep external moisture, for example liquid water, from penetrating though the gel cover into gel 114A while allowing moisture vapor from the gel, for example moisture vapor from the skin, to transmit through the gel cover.

In many embodiments, cover 162 can encase the flex PCB and/or electronics and can be adhered to at least one of the electronics, the flex PCB or adherent patch 110, so as to protect at least the electronics components and the PCB. Cover 162 can attach to adherent patch 110 with adhesive 116B. Cover 162 can comprise many known biocompatible cover materials, for example silicone. Cover 162 can comprise an outer polymer cover to provide smooth contour without limiting flexibility. In many embodiments, cover 162 may comprise a breathable fabric. Cover 162 may comprise many known breathable fabrics, for example breathable fabrics as described above. In some embodiments, the breathable cover may comprise a breathable water resistant cover. In some embodiments, the breathable fabric may comprise polyester, nylon, polyamide, and/or elastane (Spandex) to allow the breathable fabric to stretch with body movement. In some embodiments, the breathable tape may contain and elute a pharmaceutical agent, such as an antibiotic, anti-inflammatory or antifungal agent, when the adherent device is placed on the patient.

The breathable cover 162 and adherent patch 110 comprise breathable tape can be configured to couple continuously for at least one week the at least one electrode to the skin so as to measure breathing of the patient. The breathable tape may comprise the stretchable breathable material with the adhesive and the breathable cover may comprises a stretchable water resistant material connected to the breathable tape, as described above, such that both the adherent patch and cover can stretch with the skin of the patient. Arrows 182 show stretching of adherent patch 110, and the stretching of adherent patch can be at least two dimensional along the surface of the skin of the patient. As noted above, connectors 122A, 122B, 122C and 122D between PCB 130 and electrodes 112A, 112B, 112C and 112D may comprise insulated wires that provide strain relief between the PCB and the electrodes, such that the electrodes can move with the adherent patch as the adherent patch comprising breathable tape stretches. Arrows 184 show stretching of cover 162, and the stretching of the cover can be at least two dimensional along the surface of the skin of the patient. Cover 162 can be attached to adherent patch 110 with adhesive 116B such that cover 162 stretches and/or retracts when adherent patch 110 stretches and/or retracts with the skin of the patient. For example, cover 162 and adherent patch 110 can stretch in two dimensions along length 170 and width 174 with the skin of the patient, and stretching along length 170 can increase spacing between electrodes. Stretching of the cover and adherent patch 110, for example in two dimensions, can extend the time the patch is adhered to the skin as the patch can move with the skin such that the patch remains adhered to the skin. Electronics housing 160 can be smooth and allow breathable cover 162 to slide over electronics housing 160, such that motion and/or stretching of cover 162 is slidably coupled with housing 160. The printed circuit board can be slidably coupled with adherent patch 110 that comprises breathable tape 110T, such that the breathable tape can stretch with the skin of the patient when the breathable tape is adhered to the skin of the patient, for example along two dimensions comprising length 170 and width 174. Electronics components 130 can be affixed to printed circuit board 120, for example with solder, and the electronics housing can be affixed over the PCB and electronics components, for example with dip coating, such that electronics components 130, printed circuit board 120 and electronics housing 160 are coupled together. Electronics components 130, printed circuit board 120, and electronics housing 160 are disposed between the stretchable breathable material of adherent patch 110 and the stretchable water resistant material of cover 160 so as to allow the adherent patch 110 and cover 160 to stretch together while electronics components 130, printed circuit board 120, and electronics housing 160 do not stretch substantially, if at all. This decoupling of electronics housing 160, printed circuit board 120 and electronic components 130 can allow the adherent patch 110 comprising breathable tape to move with the skin of the patient, such that the adherent patch can remain adhered to the skin for an extended time of at least one week, for example two or more weeks.

An air gap 169 may extend from adherent patch 110 to the electronics module and/or PCB, so as to provide patient comfort. Air gap 169 allows adherent patch 110 and breathable tape 110T to remain supple and move, for example bend, with the skin of the patient with minimal flexing and/or bending of printed circuit board 120 and electronic components 130, as indicated by arrows 186. Printed circuit board 120 and electronics components 130 that are separated from the breathable tape 110T with air gap 169 can allow the skin to release moisture as water vapor through the breathable tape, gel cover, and breathable cover. This release of moisture from the skin through the air gap can minimize, and even avoid, excess moisture, for example when the patient sweats and/or showers.

The breathable tape of adherent patch 110 may comprise a first mesh with a first porosity and gel cover 180 may comprise a breathable tape with a second porosity, in which the second porosity is less than the first porosity to minimize, and even inhibit, flow of the gel through the breathable tape. The gel cover may comprise a polyurethane film with the second porosity.

In many embodiments, the adherent device comprises a patch component and at least one electronics module. The patch component may comprise adherent patch 110 comprising the breathable tape with adhesive coating 116A, at least one electrode, for example electrode 114A and gel 114. The at least one electronics module can be separable from the patch component. In many embodiments, the at least one electronics module comprises the flex printed circuit board 120, electronic components 130, electronics housing 160 and cover 162, such that the flex printed circuit board, electronic components, electronics housing and cover are reusable and/or removable for recharging and data transfer, for example as described above. In many embodiments, adhesive 116B is coated on upper side 110A of adherent patch 110B, such that the electronics module can be adhered to and/or separated from the adhesive component. In specific embodiments, the electronic module can be adhered to the patch component with a releasable connection, for example with Velcro™, a known hook and loop connection, and/or snap directly to the electrodes. Two electronics modules can be provided, such that one electronics module can be worn by the patient while the other is charged, as described above. Monitoring with multiple adherent patches for an extended period is described in U.S. Pat. App. No. 60/972,537, the full disclosure of which has been previously incorporated herein by reference. Many patch components can be provided for monitoring over the extended period. For example, about 12 patches can be used to monitor the patient for at least 90 days with at least one electronics module, for example with two reusable electronics modules.

At least one electrode 112A can extend through at least one aperture 180A in the breathable tape 110 and gel cover 180.

In some embodiments, the adhesive patch may comprise a medicated patch that releases a medicament, such as antibiotic, beta-blocker, ACE inhibitor, diuretic, or steroid to reduce skin irritation. The adhesive patch may comprise a thin, flexible, breathable patch with a polymer grid for stiffening. This grid may be anisotropic, may use electronic components to act as a stiffener, may use electronics-enhanced adhesive elution, and may use an alternating elution of adhesive and steroid.

FIG. 1K shows at least one electrode 190 configured to electrically couple to a skin of the patient through a breathable tape 192. In many embodiments, at least one electrode 190 and breathable tape 192 comprise electrodes and materials similar to those described above. Electrode 190 and breathable tape 192 can be incorporated into adherent devices as described above, so as to provide electrical coupling between the skin and electrode through the breathable tape, for example with the gel.

Second adherent patient device 100J and third adherent patient device 100A may comprise components similar to adherent patient device 100, described above. The processor of adherent patient device 100, described above may comprise a system controller to control communication and/or actions of first adherent patient device 100J and second device 100A, for example data collection and transmission. In many embodiments, data collected from second adherent patient device 100J and third adherent patient device 100A is sent wirelessly to device 100, which device 100 transmits the data to the intermediate device. In some embodiments, adherent patient device 100, second adherent patient device 100J and third adherent patient device 100A can each communicate data wirelessly with the intermediate device and may each receive instructions from the intermediate device.

FIG. 2 shows an exemplary method 200 of monitoring at least one patient, for example a plurality of patients. Method 200 can be performed with the monitoring system described above. A step 205 adheres a monitoring device to a patient. Each of the patient worn devices may be similar to adherent patient device 100 as described above. A step 210 measures patient data, for example, the parameters described above. The patient worn device performs a step 215 to transmit a unique identifier, such as a serial number, to an intermediate device, for example, a gateway or intermediate device 102 as described above. The identifier may be transmitted via, for example, a wireless connection, a cellular connection, a ZigBee connection, a BlueTooth connection, an Internet connection, an intranet connection, a wire connection, a cable connection or the like. The patient worn device performs a step 220 to request pairing with the gateway or intermediate device. Often, the gateway or intermediate device may include a list and/or range of allowed devices, patients, and/or device serial numbers, for instance an approved patient list, as previously described. The gateway or intermediate device performs a step 225 to receive the approved patient list. The gateway or intermediate device performs a logic step 230 in which a sub-step 235 determines whether the identifier is in the approved patient list and/or within the range of allowed devices. If the identifier is not in the approved patient list or within the range of allowed devices, the gateway or intermediate device performs step 240 which excludes communication between the patient worn device with the identifier in question and the gateway. If the identifier is in the approved patient list or within the range of allowed devices, the gateway or intermediate device performs step 245 which allows pairing or paired communication between the gateway and the patient worn device. If pairing is allowed, patient worn device performs a step 250 to exchange a link key between the patient worn device and the gateway or intermediate device. A step 245 pairs the patient device with the gateway. The exchanged link key allows the patient worn device to pair with the gateway in step 255. The patient worn device performs a step 260 to encrypt the patient data. The patient worn device performs a step 265 to transmit the encrypted patient data to the gateway or intermediate device. The gateway or intermediate device receives the encrypted patient data in a step 270 and decrypt the encrypted patient data in a step 275. The exchanged link key may enable the gateway or intermediate device to decrypt the patient data.

The gateway or intermediate device performs a step 280 which transmit the patient data to a backend server or system at a remote center and/or site as previously described. The patient data may also be decrypted by the backend server or system and transmitted as encrypted data from the patient worn device to the gateway or intermediate device to the backend server or system. The approved patient list may be updated by the backend system or server with a step 285. Once the approved device list or range of allowed device serial number has been updated, the backend system or server performs a step 290 to send the updated approved patient or device list or range of allowed devices to a gateway or intermediate device. Gateway or intermediate device may then repeat logic step 230 and so forth.

It should be appreciated that the specific steps illustrated in FIG. 2 provide a particular method of monitoring a patient, according to an embodiment of the present invention. Other sequences of steps may also be performed according to alternative embodiments. For example, alternative embodiments of the present invention may perform the steps outlined above in a different order. Moreover, the individual steps illustrated in FIG. 2 may include multiple sub-steps that may be performed in various sequences as appropriate to the individual step. Furthermore, additional steps may be added or removed depending on the particular applications. One of ordinary skill in the art would recognize many variations, modifications, and alternatives.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A system for monitoring a patient, the system comprising:
   a server system having a tangible medium configured to store and transmit gateway specific patient device list;
   a patient device adapted to be coupled to the patient to measure patient data, the patient device comprising a communications module configured to transmit a device identifier; and
   a gateway configured to communicate with the server system and the patient device, the gateway configured to receive the device identifier from the patient device and to receive a request from the patient device to pair with the gateway, and wherein the gateway is further configured transmit a gateway identifier to the server system and to receive the gateway specific patient device list, which includes a list of approved device identifiers associated with the gateway identifier, from the server system upon receipt of the request from the patient device to pair with the gateway, wherein the patient device provides the gateway with a link key if successfully paired with the gateway, wherein at least one of the server system, the patient device or the gateway is configured to determine an encryption key from the link key and wherein the patient device is configured to encrypt the patient data for transmission with the encryption key.

2. The system of claim 1, wherein the gateway is further configured to allow pairing between the patient device and the gateway only if the device identifier received from the patient device appears in the list of approved device identifiers received from the server system.

3. The system of claim 1, wherein successful pairing of the patient device with a gateway provides a dedicated connection from the patient device to a backend server system via the gateway.

4. The system of claim 1, wherein the server system maintains a master approved patient device list for each gateway connected to the server system, wherein the master approved patient device list identifies the device identifiers associated with each gateway.

5. The system of claim 4, wherein the list of approved device identifiers received by the gateway includes the entire master approved patient device list.

6. The system of claim 4, wherein the list of approved device identifiers received by the gateway includes only those patient devices allowed to pair with the gateway.

7. The system of claim 1, wherein the list of approved device identifiers provided to the gateway includes a range of identifiers, wherein the patient device is paired with the gateway if the device identifier associated with the patient device is within the range of identifiers.

8. A method of communicating patient monitoring data, the method comprising:
   receiving, at a gateway from a patient device via a first electronic communication link, a device identifier transmitted by the patient device;
   receiving, at the gateway from the patient device via the first electronic communication link, a request to pair the patient device to the gateway;
   upon receipt of the request to pair the patient device to the gateway, performing a step to provide to a remote server system via a second electronic communication link a unique gateway identifier and receive in response to the unique gateway identifier a list of approved device identifiers associated with the unique gateway identifier from the remote server system via the second electronic communication link
   receiving, at the gateway paired with the patient device via the first electronic communication link, a link key associated with the patient device;
   measuring patient data using the patient device;
   encrypting, at the patient device, the measured patient data using the link key;
   communicating the measured patient data to the gateway paired with the patient device via the first electronic communication link, wherein the measured patient data communicated to the gateway is encrypted; and
   decrypting, at the gateway, the encrypted measured patient data using the link key.

9. The method of claim 8, further comprising:
   comparing the device identifier received from the patient device with the list of approved device identifiers received from the server system; and
   allowing pairing between the patient device and the gateway only when the device identifier received from the patient device appears in the list of approved device identifiers.

10. The method of claim 8, further comprising:
    preventing communication from the patient device to the gateway if the device identifier received from the patient device does not appear in the list of approved device identifiers.

11. The method of claim 8, further comprising communicating the measured patient data received at the gateway to the remote server via the second electronic communication link.

12. The method of claim 11, wherein the gateway includes in the measured patient data communicated to the remote server the device identifier associated with the patient device that measured the patient data.

13. The method of claim 8, further comprising receiving, at the gateway via the second electronic communication link, an updated list of approved device identifiers from the remote server.

* * * * *